United States Patent
Swanson et al.

(10) Patent No.: US 6,383,958 B1
(45) Date of Patent: May 7, 2002

(54) NONWOVEN SHEETS, ADHESIVE ARTICLES, AND METHODS FOR MAKING THE SAME

(76) Inventors: David P. Swanson; Robert J. Maki; Elda G. Bloemendal, all of P.O. Box 33427, St. Paul, MN (US) 55133-3427

( * ) Notice: Subject to any disclaimer, the term of this patent is extended or adjusted under 35 U.S.C. 154(b) by 0 days.

(21) Appl. No.: 09/367,509

(22) PCT Filed: Jun. 18, 1999

(86) PCT No.: PCT/US99/13862

§ 371 Date: Aug. 13, 1999

§ 102(e) Date: Aug. 13, 1999

(87) PCT Pub. No.: WO00/78883

PCT Pub. Date: Dec. 28, 2000

(51) Int. Cl.[7] .................. B32B 27/04; B32B 27/12; B32B 5/02

(52) U.S. Cl. .................. 442/151; 442/65; 442/327; 442/334; 442/336; 442/337; 442/394; 428/141; 428/196; 428/343; 428/352; 428/354

(58) Field of Search ................ 428/343, 352, 428/354, 141, 196; 442/40.1, 41.8, 65, 327, 151, 334, 336, 337, 394; D18/15

(56) References Cited

U.S. PATENT DOCUMENTS

| | | | |
|---|---|---|---|
| 2,464,301 A | 3/1949 | Francis | 154/46 |
| 2,708,192 A | 5/1955 | Joesting et al. | 117/122 |
| RE24,906 E | 12/1960 | Ulrich | 206/59 |
| 3,121,021 A | 2/1964 | Copeland | 117/122 |
| 3,143,208 A | 8/1964 | Sizemore, Jr. | 206/56 |
| 3,234,062 A | 2/1966 | Morris | 156/104 |
| 3,449,184 A | 6/1969 | Balk | 156/105 |
| 3,485,706 A | 12/1969 | Evans | 161/72 |
| 3,507,943 A | 4/1970 | Such et al. | 264/103 |
| 3,575,782 A | 4/1971 | Hansen | 161/141 |
| 3,681,179 A | 8/1972 | Theissen | 161/4 |
| 3,737,368 A | 6/1973 | Such et al. | 161/123 |
| 3,772,262 A | 11/1973 | Clementi | 260/94.7 |
| 3,825,379 A | 7/1974 | Lohkamp et al. | 425/72 |
| 3,849,241 A | 11/1974 | Butin et al. | 161/169 |
| 3,867,222 A | 2/1975 | Plant et al. | 156/107 |
| 3,908,650 A | 9/1975 | Dunshee et al. | 128/156 |
| 4,035,549 A | 7/1977 | Kennar | 428/409 |

(List continued on next page.)

FOREIGN PATENT DOCUMENTS

| | | |
|---|---|---|
| DE | 3926897 | 3/1991 |
| DE | 19522792 | 6/1995 |
| DE | 4406978 | 9/1995 |

(List continued on next page.)

OTHER PUBLICATIONS

Patent Abstracts of Japan, vol. 1995, No. 01, Feb. 28, 1995 & JP06285978, Oct. 11, 1994 (abstract).

(List continued on next page.)

*Primary Examiner*—Terrel Morris
*Assistant Examiner*—Norca L. Torres
(74) *Attorney, Agent, or Firm*—Eloise J. Maki; Doreen S. L. Gwin

(57) ABSTRACT

Nonwoven sheet materials, and adhesive articles formed therefrom are provided that are made with fibers, preferably tensilized nonfracturable staple fibers, and binder fibers, and formed from a combination of interbonding, smooth roll calendering, and pattern embossing techniques. These sheet materials are especially useful as tape backings that are finger tearable in the cross web and the down web directions and also possess a number of other desirable properties, including acceptable tensile strength and enhanced overtaping, for example. A nonwoven sheet material, and adhesive article including the same, can include an embossed pattern having a variety of discontinuous configurations to enhance tearing properties in both the down web and cross web directions.

58 Claims, 4 Drawing Sheets

U.S. PATENT DOCUMENTS

| | | | | |
|---|---|---|---|---|
| 4,083,913 A | | 4/1978 | Marshall | 264/121 |
| 4,112,177 A | | 9/1978 | Salditt et al. | 428/304 |
| 4,148,958 A | | 4/1979 | Tischer et al. | 428/196 |
| 4,181,752 A | | 1/1980 | Martens et al. | 427/54.1 |
| 4,188,436 A | | 2/1980 | Ellis et al. | 428/198 |
| 4,234,533 A | | 11/1980 | Langlands | 264/261 |
| 4,292,360 A | * | 9/1981 | Riedel et al. | 424/171 |
| 4,299,639 A | | 11/1981 | Bayer | 156/104 |
| 4,303,485 A | | 12/1981 | Levens | 204/159.24 |
| 4,303,724 A | | 12/1981 | Sergeant et al. | 428/229 |
| 4,329,384 A | | 5/1982 | Vesley et al. | 428/40 |
| 4,330,590 A | | 5/1982 | Vesley | 428/336 |
| 4,341,213 A | | 7/1982 | Cohen | 128/284 |
| 4,341,576 A | | 7/1982 | Lewis | 156/106 |
| 4,358,329 A | | 11/1982 | Masuda | 156/106 |
| 4,362,587 A | | 12/1982 | Baudin et al. | 156/87 |
| 4,379,201 A | | 4/1983 | Heilmann et al. | 428/345 |
| 4,380,564 A | * | 4/1983 | Cancio et al. | 428/167 |
| 4,385,951 A | | 5/1983 | Pressau | 156/105 |
| 4,386,991 A | | 6/1983 | Shiomi et al. | 156/308.6 |
| 4,431,471 A | | 2/1984 | Mertens et al. | 156/103 |
| 4,451,314 A | | 5/1984 | Knoke et al. | 156/148 |
| 4,452,840 A | | 6/1984 | Sato et al. | 428/156 |
| 4,465,729 A | | 8/1984 | Cancio et al. | 428/167 |
| 4,490,425 A | | 12/1984 | Knoke et al. | 428/90 |
| 4,490,427 A | | 12/1984 | Grant et al. | 428/107 |
| 4,511,615 A | | 4/1985 | Ohta | 428/198 |
| 4,543,283 A | | 9/1985 | Curtze et al. | 428/38 |
| 4,554,324 A | | 11/1985 | Husman et al. | 525/301 |
| 4,569,960 A | | 2/1986 | Blake | 524/145 |
| 4,599,274 A | | 7/1986 | Ando et al. | 428/442 |
| 4,619,979 A | | 10/1986 | Kotnour et al. | 526/88 |
| 4,639,390 A | | 1/1987 | Shoji | 428/195 |
| 4,671,913 A | | 6/1987 | Gen et al. | 264/171 |
| 4,728,571 A | | 3/1988 | Clemens | 428/352 |
| 4,731,277 A | | 3/1988 | Groitzsch et al. | 428/137 |
| 4,737,559 A | | 4/1988 | Kellen et al. | 526/291 |
| 4,772,499 A | | 9/1988 | Greenway | 428/43 |
| 4,833,179 A | | 5/1989 | Young et al. | 522/183 |
| 4,843,134 A | | 6/1989 | Kotnour et al. | 526/318.4 |
| 4,844,973 A | | 7/1989 | Konishi et al. | 428/286 |
| 4,925,725 A | | 5/1990 | Endo et al. | 428/156 |
| 4,973,513 A | | 11/1990 | Riedel | 428/252 |
| 4,999,235 A | * | 3/1991 | Lunn et al. | 428/156 |
| 5,016,331 A | | 5/1991 | Dilo | 28/115 |
| 5,091,258 A | | 2/1992 | Moran | 428/437 |
| 5,100,963 A | | 3/1992 | Lin | 525/221 |
| 5,147,485 A | | 9/1992 | Gajewski et al. | 156/104 |
| 5,178,933 A | | 1/1993 | Yoshida et al. | 428/207 |
| 5,180,756 A | | 1/1993 | Rehmer et al. | 522/35 |
| 5,190,992 A | | 3/1993 | Kato et al. | 522/180 |
| 5,254,388 A | | 10/1993 | Melby et al. | 428/120 |
| 5,268,049 A | | 12/1993 | Marriott et al. | 156/99 |
| 5,362,801 A | | 11/1994 | Amici et al. | 525/57 |
| 5,382,400 A | | 1/1995 | Pike et al. | 264/168 |
| 5,407,971 A | | 4/1995 | Everaerts et al. | 522/35 |
| 5,425,977 A | | 6/1995 | Hopfe | 428/141 |
| 5,436,283 A | | 7/1995 | Okada et al. | 523/120 |
| 5,445,890 A | | 8/1995 | Bayha et al. | 428/431 |
| 5,455,103 A | | 10/1995 | Hoagland et al. | 428/167 |
| 5,461,103 A | | 10/1995 | Bafford et al. | 524/460 |
| 5,487,412 A | | 1/1996 | Matthews et al. | 138/149 |
| 5,496,603 A | * | 3/1996 | Riedel et al. | 428/40 |
| 5,521,229 A | | 5/1996 | Lu et al. | 522/40 |
| 5,536,347 A | | 7/1996 | Moran | 156/103 |
| 5,547,736 A | | 8/1996 | Simon et al. | 428/143 |
| 5,595,818 A | | 1/1997 | Hopfe et al. | 428/327 |
| 5,620,779 A | | 4/1997 | Levy et al. | 428/167 |
| 5,624,973 A | | 4/1997 | Lu et al. | 522/40 |
| 5,631,073 A | | 5/1997 | Riedel et al. | 442/364 |
| 5,637,646 A | | 6/1997 | Ellis | 525/309 |
| 5,679,190 A | | 10/1997 | Riedel et al. | 156/62.2 |
| 5,741,542 A | | 4/1998 | Williams et al. | 427/208.4 |
| 5,750,134 A | | 5/1998 | Scherrer et al. | 424/434 |
| 5,804,610 A | | 9/1998 | Hamer et al. | 522/182 |
| 5,969,069 A | | 10/1999 | Su et al. | 526/318.44 |
| 5,976,690 A | | 11/1999 | Williams et al. | 428/345 |

FOREIGN PATENT DOCUMENTS

| | | |
|---|---|---|
| DE | 4432368 | 3/1996 |
| DE | 196 28 999 | 3/1998 |
| EP | 0 099 087 | 1/1984 |
| EP | 0 056 719 B1 | 5/1987 |
| EP | 0 525 403 A1 | 2/1993 |
| EP | 670338 | 9/1995 |
| EP | 0 701 822 | 3/1996 |
| EP | 0 710 545 A1 | 5/1996 |
| EP | 554832 B | 7/1996 |
| EP | 853092 | 7/1998 |
| GB | 2 155 856 | 10/1985 |
| JP | 51-89540 | 8/1976 |
| JP | 96073826 | 3/1996 |
| WO | WO89/12618 | 12/1989 |
| WO | WO92/04418 | 3/1992 |
| WO | WO93/10177 | 5/1993 |
| WO | WO95/27014 | 10/1995 |
| WO | WO97/07161 | 2/1997 |
| WO | WO98/03208 | 1/1998 |
| WO | WO98/29516 | 7/1998 |
| WO | WO99/14415 | 3/1999 |

OTHER PUBLICATIONS

Nichols, R. T. and R. M. Sowers, "Laminated Materials, Glass," *Kirk–Othmer Encyclopedia of Chemical Technology*, 4th Ed., pp. 1059–1074, 1995.

Sung Gun Chu, Chapter 8, *Handbook of Pressure Sensitive Adhesive Technology*, Second Edition, Donatas Satas, Editor, pp. 158–203, 1989.

Masters, K., *Spray Drying: An Introduction to Principles, Operational Practice, and Application*, 2nd Edition, Wiley, NY, 1976, pp 74–93.

Satas, D., *The Handbook of Pressure Sensitive Adhesive Technology*, 2nd Edition, Van Nostrand Reinhold, NY, 1989, pp 172–173.

ASTM Designation: D 3654M–88 (Reapproved 1993), Standard Test Method for Holding Power of Pressure Sensitive Tapes (Metric).

Fox, T. G., Bulletin of the American Physical Society (ser. 2), 12.3, J5 (1956).

Kirk–Othmer Encyclopedia of Chemical Technology, 4th Edition, John Wiley & Sons, NY, vol. 6, 1993, pp 635–636.

Derwent Abstract for JP 08 295850A.

* cited by examiner

NONWOVEN SHEETS, ADHESIVE ARTICLES, AND METHODS FOR MAKING THE SAME

FIELD OF THE INVENTION

The present invention relates to nonwoven sheets, and adhesive articles made therefrom, and in particular, to nonwoven sheet materials and adhesive articles that exhibit enhanced tear characteristics.

BACKGROUND OF THE INVENTION

Nonwoven sheet materials are often used as the backing or web component of tapes and the like. These tapes are commonly used in the health-care industry for affixation of a variety of articles, such as dressings and tubings, and as backings and affixation materials for pre-made dressings, such as first-aid dressings and island-type dressings. They are also commonly used as affixation materials on certain types of products, such as diagnostic electrodes, surgical grounding plates, and monitoring electrodes.

Tapes formed from nonwoven sheet materials fall into two general categories based on performance needs. Category I includes sheet materials, and tapes made therefrom, that can be torn in the cross machine or cross web direction. However, these materials often cannot be torn cleanly, and therefore, display uneven or irregular torn edges. On the other hand, category II includes those sheet materials and tapes that, for practical purposes, cannot be torn in either the down web direction or the cross web direction.

In general, category I nonwoven materials are predominantly comprised of cellulosic fibers, and exhibit a down web direction to cross web direction tensile strength ratio of less than 2.5 to 1. Cellulosic fibers are inherently fracturable (i.e., are easily broken under stress), as opposed to many synthetic, polymeric fibers, that are essentially nonfracturable.

The cellulosic fibers used in category I sheet materials are typically bonded together by a chemical binder that immobilizes, or partially immobilizes the fibers. In addition, the chemical binder increases the density of the sheet materials, and provides other advantageous properties, such as enhanced tensile strength, elongation at break, Hand (i.e., conformability), decreased fuzzing, and the specific tear characteristics noted above. However, these advantageous properties are rapidly compromised when the sheet material becomes wet, and especially when it becomes saturated with water or other water-based fluids.

Category II materials are most frequently formed from essentially nonfracturable synthetic fibers, and are either thermally, mechanically, or chemically bonded to provide structural integrity to the sheet materials. These materials can display enhanced tensile strength, elongation, Hand, and depending on their particular construction. For example, mechanically bonded category II materials are typically softer and more fuzzy, in comparison with the chemically bonded materials, that tend to be stiffer and less fuzzy. However, in virtually all instances, category II sheet materials are essentially incapable of being torn in the cross web direction, and thus, do not meet the affixation requirements of the health-care industry.

Both category I and II nonwoven sheet materials and tapes enjoy reasonably extensive use in the wound treatment and medical device affixation areas of the practice of health-care. However, neither type of material has been able to make significant advances into the broader areas of the health-care market due to their inherent limitations.

Category I materials lack water resistance, and are unable to provide sufficient strength, while still maintaining softness, Hand and/or reasonable tear characteristics. Strength can be improved by changing the down web direction to cross web direction orientation ratios of the fibers at the expense of tear. In addition, strength can also be improved by increasing the basic fiber content and weight at the expense of Hand and tear.

Altering the characteristics of category II sheet materials made with synthetic polymer fibers is even more restrictive. Reasonably good tear can only be achieved by utilizing fibers that make the sheet materials, and resulting tapes, very stiff. In so doing, the fiber-to-fiber bonds are essentially locked-up, thereby reducing fabric conformability, and providing a tear which is extremely difficult, and not satisfactory in terms of ragged edges and failure to tear straight.

Many attempts have been made in recent years to enhance the characteristics of category I and II materials, or to provide nonwoven sheet materials and tapes with the desirable characteristics of both category I and II materials. In so doing, different fiber types, contents, and weights of the nonwoven sheet materials have been tried. In addition, various bonding techniques, including bonding with a chemical sizing agent, physical entanglement of the web (e.g., hydroentanglement) and thermal bonding, such as through thermal embossing, have been employed. See, e.g., U.S. Pat. No. 4,973,513 (chemical bonding with LAB), U.S. Pat. No. 4,341,213 (chemical bonding to increase strength and flammability), U.S. Pat. No. 4,772,499 (hydroentanglement and partial chemical bonding), U.S. Pat. No. 3,737,368, and U.S. Pat. No. 3,507,943 (thermal embossing with engraved rollers).

For example, U.S. Pat. No. 3,121,021 discloses surgical adhesive tape formed from a tissue backing of rayon staple fibers coated with a non-tacky hydrophobic rubbery fiber-sizing polymer. The polymer-bonded backing is coated with a thin layer of pressure-sensitive adhesive that exhibits a microporous structure after drying. Incorporation of the hydrophobic rubbery fiber-sizing polymer serves to increase the water repellency, and thus, the wet strength of this category I material. Similarly, U.S. Pat. No. 4,112,177 provides essentially the same nonwoven backing as with U.S. Pat. No. 3,121,021, however, multiple adhesive layers are applied to the backing to improve the overall adhesive properties of the tapes formed therefrom. A further example of a porous, double-coated adhesive tape is disclosed in U.S. Pat. No. 4,844,973.

U.S. Pat. No. 4,292,360 discloses a multi-ply nonwoven sheet material that can be used to make pressure-sensitive adhesive tapes. The sheet materials are comprised of two nonwoven webs that are overlaid and bonded together by a rewettable chemical binder. The nonwoven webs can be formed of any type or combination of staple fibers, either alone, or in combination with binder fibers. In addition to the chemical binder, the sheet materials can also be optionally calendered or embossed.

U.S. Pat. No. 3,908,650 discloses a microporous tape formed from a nonwoven web coated on one side with a porous layer of a pressure-sensitive adhesive, and on the other with a porous thermoplastic film. The fibers adjacent the thermoplastic layer are, at least to some extent, water repellent. Optionally, the fibrous web may be thermally bonded or chemically bonded with a sizing agent. Utilization of the thermoplastic layer imparts increased abrasion and soil resistance to the overall tape.

U.S. Pat. No. 4,772,499 discloses a nonwoven web that is readily tearable in the cross web direction. The tearability of the web is enhanced by pattern bonding portions of the web with a bonding agent. After drying, the web is stated to be readily tearable in the cross web direction along the non-bonded portions of the web. Also, U.S. Pat. No. 4,303,724 discloses the use of texturized or false twist yarns in the filing of nonwoven fabrics to improve their tear characteristics.

German Patent No. DE 1 595 300 discloses nonwoven fabrics formed from wet-laid webs that are hot calendered while the web still retains from 10% to 40% by weight residual moisture. These webs are comprised of unstretched polyester binder fibers, and optionally can include stretched polyester fibers, polyacrylamide fibers, and/or polyamide imide fibers. Further examples of thermal bonding as the principal means of reinforcing nonwoven materials can also be found in U.S. Pat. Nos. 4,731,277, 4,639,390, 4,511,615, 4,490,427, and 4,083,913. In addition, thermal bonding can be brought about by embossing such sheet materials using heated, engraved rollers. See, e.g., U.S. Pat. Nos. 3,737,368 and 3,507,943.

U.S. Pat. No. 4,490,425 discloses a soft and fluffy nonwoven fabric formed by thermal bonding staple fibers, endless fibers, or both, and needle puncturing (i.e., tacking) one or both sides of the fabric to form the fluffy surface. Thereafter, one or more of the sides are coated with a thermal adhesive to yield a fabric useable as an interlining in various garments. Similar interlining materials and methods of their preparation are also disclosed in U.S. Pat. Nos. 4,451,314 and 4,148,958.

None of the previously described sheet materials or tapes has successfully combined the advantages of category I and II materials, while eliminating their shortcomings. In fact, to date, no single nonwoven sheet material, or tape made therefrom, exhibits enhanced strength, enhanced overtaping, and ease of tear in any direction, while maintaining reasonable Hand values.

SUMMARY OF THE INVENTION

The present invention provides nonwoven sheet materials, and tapes formed therefrom, made with fibers, preferably tensilized nonfracturable staple fibers, and binder fibers, and formed from a combination of interbonding, smooth roll calendering, and pattern embossing techniques. These sheet materials are especially useful as tape backing fabrics that are finger tearable in the cross web and the down web directions within the requirements of the user community, and also possess a number of other desirable properties, including acceptable tensile strength and enhanced overtaping, for example.

One aspect of the present invention provides a pressure-sensitive adhesive article including nonwoven backing having a first surface and a second surface; and a pressure sensitive adhesive coated on the first surface of the backing, wherein the backing comprises an embossed pattern on a first fibrous web. In accordance with the present invention, the embossed pattern is selected from the group consisting of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction. A pressure sensitive adhesive article according to the present invention can also include a low adhesion backsize composition coated on the second surface of the backing and/or a release liner on the pressure sensitive adhesive coated on the first surface of the backing. Typically, the pressure sensitive adhesive is selected from the group consisting of a rubber-based adhesive, a water-based adhesive, a solvent-based adhesive, a hot-melt adhesive, and a combination thereof. A pressure sensitive adhesive article in accordance with the present invention can also include a backing that further includes a second nonwoven web, preferably laminated to the first nonwoven web.

Another aspect of the present invention provides a nonwoven sheet article including an embossed pattern on a fibrous web selected from the group consisting of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction.

In any of the articles according to the present invention, the fibrous web preferably includes nonfracturable staple fibers, binder fibers, and a binding agent.

Preferably, the plurality of depressions is up to about 28% of a total surface area of the backing.

Each of the plurality of depressions can be in a shape selected from the group consisting of a diamond, a rectangle, a circle, an oval, a triangle, a "+" sign, a "<" sign, a ">" sign, and a combination thereof. Preferably, the distance between two consecutive depressions in a first direction is about 0.51 mm to about 0.36 mm and the distance between two consecutive depressions in a second direction is about 0.51 mm to about 3.6 mm. Preferably, the first direction and the second direction are substantially normal to one another.

In one embodiment, each of the plurality of depressions in a row is in a shape selected from the group consisting of alternating "+" signs and "−" signs. In another embodiment, each of the plurality of depressions is a "+" sign and the plurality of depressions is about 15% to about 22% of a total surface area of the backing. In yet another embodiment, the plurality of depressions is a combination of a "+" sign and a "−" sign and the plurality of depression is about 15% to about 20% of a total surface area of the backing. In a further embodiment, the plurality of depressions is a combination of a "−" sign and a "|" such that the plurality of depressions is about 15% to about 22% of a total surface area of the backing. In yet a further embodiment, the plurality of depressions is a combination of a "+" sign and a "−" sign such that the plurality of depressions is about 15% to about 20% of a total surface area of the backing.

A further aspect of the present invention provides a method for making a nonwoven sheet material that includes forming a randomly interlaced fibrous web of tensilized nonfracturable staple fibers and binder fibers; pattern embossing the fibrous web with a pattern selected from the group consisting of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction; subsequent to pattern embossing, smooth roll calendering the fibrous web; and subsequent to smooth roll calendering, uniformly interbonding the fibrous web throughout using a chemical bonding agent.

Yet a further aspect of the present invention provides a method for making a nonwoven sheet material that includes forming a randomly interlaced fibrous web of tensilized nonfracturable staple fibers and binder fibers; first smooth roll calendering the fibrous web; pattern embossing the fibrous web with a pattern selected from the group consisting of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction; and uniformly interbonding the fibrous web throughout using a chemical bonding agent, wherein smooth roll calendering is performed prior to pattern embossing or uniformly interbonding. In one embodiment, uniformly interbonding is performed prior to pattern embossing. In another embodiment, pattern embossing is performed prior to uniformly interbonding.

Preferably, the interbonding step comprises infusing the fibrous web with a water-based chemical binding agent.

A method in accordance with the present invention can also include drying the fibrous web infused with the water-based chemical bonding agent until substantially all the water is removed.

Other steps that can be included in a method in accordance with the present invention include coating a layer of pressure sensitive adhesive on a first surface of the embossed pattern web, coating a low adhesion composition on a second surface of the embossed pattern web, winding the embossed pattern web in a roll such that the pressure sensitive adhesive on the first surface of the embossed pattern web contacts a low adhesion backsize on the second surface of the embossed pattern web, and a combination thereof.

Yet another aspect of the present invention provides a method of making a pressure-sensitive adhesive article including forming a first randomly interlaced fibrous web; smooth roll calendering the fibrous web; pattern embossing the fibrous web to form an embossed pattern comprising a plurality of discontinuous depressions in a first direction and a second direction; uniformly interbonding the fibrous web throughout using a chemical bonding agent; and coating a first surface of the fibrous web with a pressure sensitive adhesive, wherein the pressure sensitive adhesive article has an overtaping value of less than about 76 mm. A method may also include other steps such as laminating a second fibrous web to the first fibrous web and coating a low adhesion backsize on a second surface of the fibrous web.

In one embodiment, pattern embossing the fibrous web occurs prior to smooth roll calendering the fibrous web and uniformly interbonding the fibrous web. In another embodiment, smooth roll calendering the fibrous web occurs prior to pattern embossing the fibrous web and uniformly interbonding the fibrous web. In yet another embodiment, uniformly interbonding the fibrous web occurs prior to pattern embossing the fibrous web.

The terms "machine direction" and "down web direction" are used interchangeably and refer to the lengthwise direction of the web. The fibers which comprise the nonwoven sheet materials are predominantly oriented in the down web direction of the nonwoven sheet materials. The terms "cross machine direction" and "cross web direction" are used interchangeably herein and refer to a direction about perpendicular to the down web direction of the nonwoven sheet materials.

As used herein, "embossed pattern" and "calendered pattern" are used interchangeably and refer to a predetermined configuration of depressions on the surface of the web. An embossed pattern is to be distinguished from a "perforated" pattern, which refers to a predetermined configuration of punctures that pass through the entire thickness of the web. Thus, an embossed pattern on a web/tape backing in accordance with the present invention is a non-perforated pattern of depressions in the surface of the web, such that the pattern is preferably discontinuous in both the down web and the cross web directions.

DETAILED DESCRIPTION OF EMBODIMENTS OF THE INVENTION

Nonwoven Sheet Materials

Figure 1:
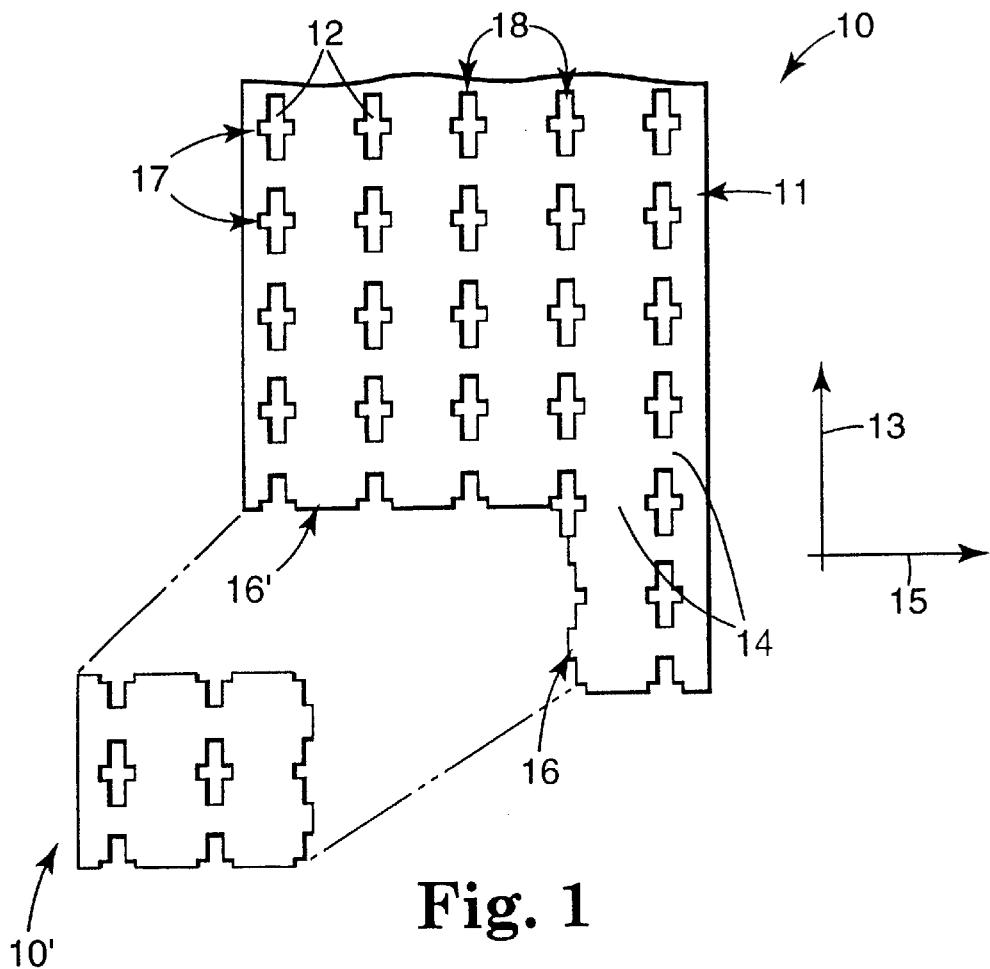
FIG. 1 is a schematic diagram of one embodiment of an embossed backing material in accordance with the present invention.

The fibrous web component of the nonwoven sheet materials and tapes according to the present invention is made in accordance with conventional methods known in the art, including wet-laid methods, dry-laid methods, such as air layering and carding, and direct-laid methods for continuous fibers, such as spunbonding and meltblowing. Examples of several methods are disclosed in U.S. Pat. No. 3,121,021 to Copeland, U,S, Pat. No. 3,575,782 to Hansen, U.S. Pat. Nos. 3,825,379, 3,849,241, and 5,382,400.

A suitable example of a fibrous web component can include tensilized nonfracturable staple fibers and binder fibers are used in the formation of the fibrous web component of the nonwoven sheet materials and tapes of the present invention, as described in U.S. Pat. Nos. 5,496,603; 5,631,073; and 5,679,190 all to Riedel et al. As used herein, "tensilized nonfracturable staple fibers" refer to staple fibers, formed from synthetic polymers, that are drawn during manufacture, such that the polymer chains substantially orient in the machine direction or down web direction of the fiber, and that will not readily fracture when subjected to a moderate breaking force. The controlled orientation of these staple fibers imparts a high degree of ordered crystallinity (e.g. generally above about 45% crystallinity) to the polymer chains comprising the fibers. Generally, the tensilized nonfracturable staple fibers of the present invention will not fracture unless subjected to a breaking force of at least 3.5 g/denier.

Nonlimiting examples of suitable tensilized nonfracturable staple fibers according to the present invention include polyester staple fibers, polyolefin staple fibers, polyamide staple fibers, polyacrylate staple fibers, polycarbonate staple fibers, polysulfone staple fibers, or combinations thereof. In accordance with the present invention, a minor amount of fracturable staple fibers, preferably less than 50% by weight, such as rayon staple fibers, acrylic staple fibers, cellulose staple fibers, cotton staple fibers, and the like.

Preferably, the tensilized nonfracturable staple fibers comprise oriented polyolefin staple fibers, such as oriented polyethylene, polypropylene, or polybutylene staple fibers, oriented polyester staple fibers, such as polyethylene terephthalate (PET), or combinations thereof. These oriented staple fibers are preferably from about 1 cm to about 10 cm, more preferably, 2 cm to 5 cm in length, and display a fineness of from about 0.1 denier to about 20 denier, more preferably from about 0.5 denier to about 5 denier, and most preferably from about 0.7 denier to about 2 denier.

In a particularly preferred embodiment, the tensilized nonfracturable staple fibers comprise oriented polyester staple fibers, such as 0.95 denier polyester (PET) staple fibers or, standard polyester staple fibers (PET), 1.2 denier polyester staple fibers, and/or 2.0 denier standard polyester staple fibers (PET).

Any type or types of binder fibers can be employed to form the fibrous web of the present invention, as long as they are capable of melt-bonding to the tensilized nonfracturable staple fibers of the fibrous web without fracturing, or substantially weakening the tensilized nonfracturable staple fibers. In this regard, it is preferable that the binder fibers be formed from one or more man-made thermoplastic polymers that are capable of melt-bonding with the tensilized nonfracturable staple fibers used in the nonwoven sheet materials and tapes of the present invention. Furthermore, the binder fibers can comprise a wide variety of binder fiber configurations that are well known in the art, including, without limitation, totally meltable binder fibers, side-by-side binder fibers, bicomponent binder fibers, elliptical core-sheath binder fibers, concentric core-sheath binder fibers, or combinations thereof.

Examples of suitable binder fibers, include, without limitation, polyester binder fibers, polyolefin binder fibers, such as thermoplastic polyethylene, polypropylene, and polybutylene binder fibers, polyamide binder fibers, or combinations thereof. These binder fibers are preferably from about 1 cm to about 20 cm, more preferably, 2 cm to 10 cm in length, and display a fineness of from about 0.1 denier to about 20 denier, more preferably from about 0.2 denier to about 10 denier, and most preferably from about 0.5 denier to about 6 denier.

In a particularly preferred embodiment, the binder fibers comprise core-sheath binder fibers containing, for example, an oriented polyester or polyolefin fiber core surrounded by an outer sheath of a meltable polyester or polyolefin resin. Specific examples of suitable core-sheath binder fibers for use in the fibrous webs of the present invention include 1.5 denier, 38 mm, crystalline polypropylene core and meltable polyethylene sheath; and 2 denier, 38 mm, oriented polyester core and meltable polyester sheath.

The weight ratio of tensilized nonfracturable staple fibers to binder fibers in the fibrous web will depend upon the application to which the nonwoven sheet materials or tapes of the present invention are to be put. In most cases, predetermined strength, tearability, and other requirements of the nonwoven sheet materials and tapes of the present invention can be obtained by balancing the quantity of high-strength, tensilized nonfracturable staple fibers against the quantity of thermoplastic binder fibers needed to insure adequate binding, and ultimately, the structural integrity of the fibrous web.

Generally, from about 95% to about 50%, preferably from about 90% to about 60% by weight of the fibrous web will be comprised of one or more varieties of tensilized nonfracturable staple fibers, while from about 50% to about 5%, preferably from about 40% to about 10% by weight of the fibrous web will be binder fibers. In a preferred aspect, the weight ratio of tensilized nonfracturable staple fibers to binder fibers will be from about 10:1 to about 1:10, more preferably from about 5:1 to about 1:1, and most preferably from about 4:1 to about 2:1.

The thickness of the nonwoven sheet materials according to the present invention is largely dependent upon the desired use. In general, a nonwoven sheet can be from about 0.04 mm to about 0.5 mm in thickness. When the desired end use of the nonwoven sheet material is as a backing for medical tape, a preferred thickness is from about 0.1 mm to about 0.4 mm. In addition, the weight of the nonwoven sheet can be from about 10 $g/m^2$ to about 100 $g/m^2$, preferably from about 15 $g/m^2$ to about 70 $g/m^2$.

In one preferred embodiment, a fibrous web includes about 60% by weight of about a 0.95 denier, 4 cm length, oriented polyester staple fiber combined with about 20% by weight of about a 2 denier, 5 cm length, polyester binder fiber, and about a 20% by weight of a rayon fiber of about 1.5 denier, 4 cm length having an average total fiber weight of about 30 $g/m^2$.

The second preferred embodiment, a fibrous web comprises essentially the same material as the first embodiment, but, instead of the rayon fiber, includes about 20% by weight of a polypropylene fiber of about 2.2 denier, 4 cm length having an average total fiber weight of about 30 $g/m^2$.

In accordance with the principles of the present invention, the fibrous web is interbonded with a chemical bonding agent, through physical entanglement, or both, and is pattern embossed to yield the nonwoven sheet materials of the present invention.

One method of interbonding the fibrous web is to physically entangle the fibers after formation of the web by conventional means well known in that art. For example, the fibrous web can be needle-tacked as described in U.S. Pat. No. 5,016,331. In an alternative, and preferred method, the fibrous web can be hydroentangled, such as described in U.S. Pat. No. 3,485,706. One such method of hydroentangling involves passing a fibrous web layered between stainless steel mesh screens (e.g., 100 mesh screen, National Wire Fabric, Star City, Ark.) at a predetermined rate (e.g., about 23 m/min) through high pressure water jets (e.g., from about 3 MPa to about 10 MPa), that impinge upon both sides of the web. Thereafter, the hydroentangled webs are dried, and can be subjected to pattern embossing and chemical binder saturation, as described herein.

All of the nonwoven sheet materials according to the present invention are pattern embossed, according to procedures well known in the art, such as those described in U.S. Pat. Nos. 2,464,301, 3,507,943, and 3,737,368. In general, the fibrous web is passed through a metal roll that is patterned (e.g., engraved) with raised and depressed areas, and a solid back-up roll, generally formed of metal or rubber. However, the fibrous web can also be fed between two patterned rolls displaying corresponding or alternating engraved areas. In either case, it is typical to supply heat to one or more of the rolls so that the fibrous web is thermally bonded along the points of pattern contact.

In a preferred embodiment, the fibrous webs according to the present invention are thermally embossed with a pattern roll and a solid back-up roll. During embossing, it is important to closely control the temperature of the pattern roll. In general, the temperature must be such that the tensilized nonfracturable staple fibers and binder fibers are thermally fused at the points of contact without fracturing the staple fibers (i.e., perforating the staple fibers), or seriously weakening the fibrous web below a useable strength level. In this regard, it is preferred to maintain the temperature of the pattern roll between about 70° C. and 220° C., more preferably between about 85° C. and 180° C. In addition, the pattern roll should contact the nonwoven sheet material at a pressure of from about 30 N/mm to about 120 N/mm, preferably about 35 N/mm to about 70 N/mm.

The particular pattern engraved on the embossing roll will depend upon the intended use for the resulting nonwoven sheet materials and tapes. One with skill in the art will recognize that a variety of pattern shapes will result in a patterned area (i.e., bond area) so long as a discontinuous embossed pattern is created in the material/tape backing after embossing. In accordance with the present invention, it is preferable that the resulting embossed pattern in material/tape backing has a bond area up to about 28% of the total surface area of the material/tape backing. More preferably, it is desirable to achieve a patterned area of about 15% to about 21% of the total surface area of the material/tape backing.

While not wishing to be bound by any particular theory, it is believed that the depressions in the embossed pattern are formed by localized melting the fibrous web in the pattern of the raised areas on the patterned embossing roll. The fibrous web is not destroyed by the process but, instead, maintains its integrity. The physical dimensions of the embossed depressions and the non-depressed area between each depression (also referred to herein as "land space") are important aspects of the present invention. Together, the depressions and the land space between each depression can form a separation line, wherein a separation line can be in the cross web direction and in the down web direction. An acceptable balance must be achieved between the competing interests of adequate tensile strength to prevent premature separation (i.e., tear) and sufficient reduction in tensile strength to ensure easy and consistent separation along a single separation line in both the cross web and down web directions. Surprisingly, it was found that an embossed pattern in a material/tape backing up to about 28% of the total surface area of the material/tape backing accomplishes this balance in both the cross web and down web directions.

Additionally, the parameters of the separation lines necessary to define performance are depression dimensions (e.g., length and width), land space dimension (typically the length of the non-depressed area between two consecutive depressions), and the ratio of the depression dimensions to land space dimension. The interdependence of these variables and the cooperational manner in which they effect performance of the material/tape backing requires that they be considered together. One with skill in the art will readily appreciate that each depression in the embossed pattern can have a variety of shapes and still exhibit easy and consistent separation along a single separation line in both the cross web and down web directions. Such shapes include, diamonds, squares, rectangles, triangles, circles, ovals, a character shape (e.g., a letter such as "V", "X", "A", and the like, as well as a symbol such as "+", "−", "<", ">", and the like) and a combination thereof.

Tensile strength of an embossed pattern in the material/tape backing in the down web direction, measured in accordance with the protocol set forth herein, is desirably at least about 8 N/cm width, preferably at least about 10 N/cm width. Tensile strength of an embossed pattern in the material/tape backing in the cross direction, measured in accordance with the protocol set forth herein, is desirably at least about 4 N/cm width, preferably at least about 6 N/cm width.

In accordance with the present invention, an embossed pattern preferably includes a plurality of depressions that are separated by a land space in a first direction and a second direction. Preferably, the arrangement of the plurality of depressions in the first direction is in at least two rows that are aligned such that columns are formed by consecutive depressions in a second direction. In one preferred configuration, a distance between two depressions in at least one column varies along the first direction. In another preferred configuration, a distance between two depressions in one column varies from a distance between two depressions in a second column.

In another embodiment of the invention, a multilayer (i.e., two or more layers) laminate can be formed. The laminate comprises the nonwoven sheet of the invention. In a preferred embodiment, the laminate consists of two layers of nonwoven sheet material bonded together by a tie layer. The tie layer may be any substance that will provide a strong bond between the layers of nonwoven sheet material. The bond should be of sufficient strength such that the layers of nonwoven sheet material will not delaminate and cannot be separated by hand when used as a tape construction. Suitable tie layers include, but are not limited to, polypropylene, polyethylene, ethylene vinyl acetate, and blends thereof. A preferred tie layer is polypropylene in the form of a film such as, for example, a 0.4 mm blown XBP-486.0 from Consolidated Film, Chippewa Falls, Wis. and a film extruded from Exxon 3445 polypropylene pellets from Exxon Chemical Co., Houston, Tex.

Additives can be incorporated into one or more of the nonwoven sheet material, the chemical binding agent, the tie layer, the LAB, and the adhesive. Suitable additives include colorants (i.e., pigments and dyes), processing aids (e.g., surfactants and foaming agents), and flattening agents (e.g., fillers and gloss imparting agents), to name a few.

Referring to FIG. 1, one embodiment of an embossed pattern 11 is shown on a material/tape backing 10. The embossed pattern 11 includes a plurality of depressions 12 that are in the shape of a "+" symbol. Separating each depression 12 is a land space 14 in both a down web direction 13 and a cross web direction 15. Preferably, the arrangement of the plurality of depressions 12 in a first direction (e.g., in a cross web direction) is in at least two rows 17 that are aligned such that columns 18 are formed by consecutive depressions 12 in a second direction (e.g., a down web direction 13). Preferably, each row 17 and each column 18 are substantially normal to one another. Consecutive depressions 12 separated by the land spaces 14 form a down web separation line 16 (i.e., along a column 18 of depressions 12) and a cross web separation line 16' (i.e., along a row 17 of depressions 12). Upon application of a tearing force, the material/tape backing can be torn to a desired size 10' along the down web separation line 16 and the cross web separation line 16'. As mentioned above, it is the cooperative relationship between the dimensions of the depressions 12 and the land spaces 14 that provide easy and consistent separation along a single separation line in both the cross web and down web directions. For example, in FIG. 1, the "+" symbol of each depression 12 has the following dimensions: a total height of about 0.91 mm, a total width of about 0.51 mm, wherein each of the segments in the "+" have a thickness of about 0.20 mm in both the down web and cross web directions. Additionally, the land space between each depression in the down web direction is about 0.36 mm and about 0.76 mm the cross web direction. Together, this embossed pattern 11 results in a total patterned area of about 15.4% of the total area of the material/tape backing. Thus, in this configuration, a distance between two depressions in at least one column varies along the first direction.

Figure 2:
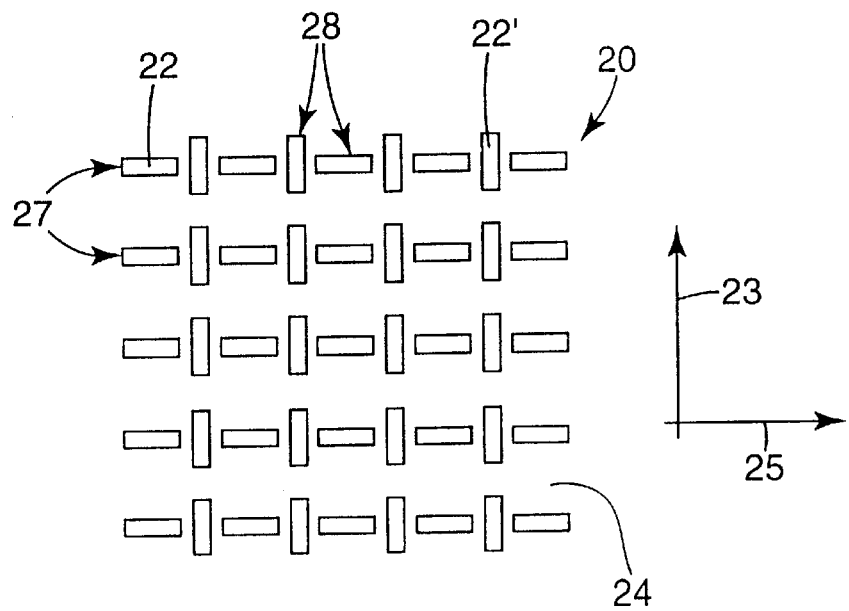
FIG. 2 is a schematic diagram of another embodiment of an embossed backing material in accordance with the present invention.

Referring to FIG. 2, another embodiment of an embossed pattern 20 is shown. The embossed pattern 20 includes a plurality of depressions 22 and 22' that are in the shape of a "–" symbol oriented along its length alternating from a down web direction 23 to a cross web direction 25. Separating each depression 22 is a land space 24 in both a down web direction 23 and a cross web direction 25. Preferably, the arrangement of the plurality of depressions 22 in a first direction (e.g., in a cross web direction 25) is in at least two rows 27 that are aligned such that columns 28 are formed by consecutive depressions 22 in a second direction (e.g., a down web direction 23). Preferably, each row 27 and each column 28 are substantially normal to one another. In FIG. 2, the "–" symbol of each depression 22 has the following dimensions: a longest dimension in the cross web direction of about 0.71 mm and a shortest dimension in the cross web direction of about 0.20 mm (resulting in an orientation of "–" of the depression when viewed along the down web direction). The "|" symbol of each depression 22' has the following dimensions: a longest dimension in the down web direction of about 0.76 mm and a shortest dimension in the down web direction of about 0.20 mm (resulting in an orientation of "|" of the depression when viewed along the down web direction). Additionally, the land space between each depression 22' in the down web direction is about 0.51 mm and about 1.07 mm for each depression 22. Each depression 22' and 22 are spaced a distance about 0.18 mm in the cross web direction. Together, this embossed pattern 20 results in a total patterned area of about 18.6% of the total area of the material/tape backing. Thus, in this configuration, a distance between two depressions in one column varies from a distance between two depressions in a second column.

Figure 3:
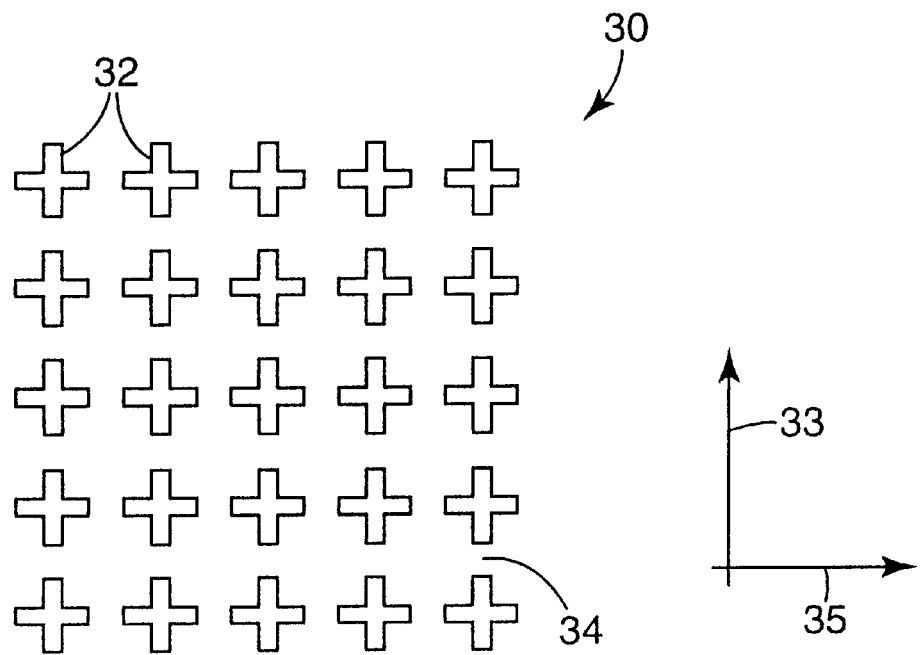
FIG. 3 is a schematic diagram of a further embodiment of an embossed backing material in accordance with the present invention.

Referring to FIG. 3, yet another embodiment of an embossed pattern 30 is shown. The embossed pattern 30 includes a plurality of depression 32 that are in the shape of a "+" symbol. Separating each depression 32 is a land space 34 in both a down web direction 33 and a cross web direction 35. In FIG. 3, the "+" symbol of each depression 32 has the following dimensions: a total height and width of about 0.91 mm, wherein each of the segments in the "+" have a thickness of about 0.20 mm in both the down web and cross web directions. Additionally, the land space between each depression in the down web and the cross web directions is about 0.36 mm. Together, this embossed pattern 30 results in a total patterned area of about 20.5% of the total area of the material/tape backing.

Figure 4:
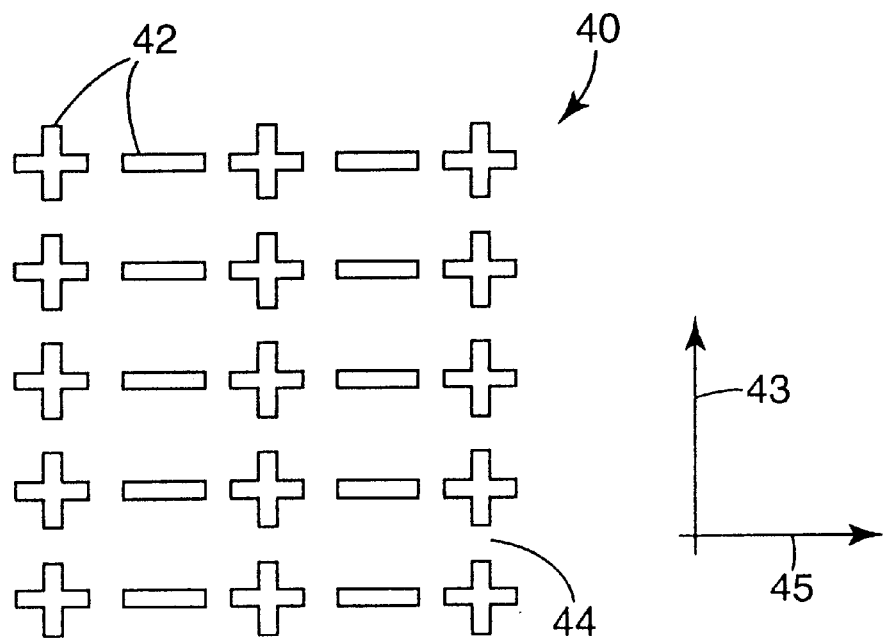
FIG. 4 is a schematic diagram of yet another embodiment of an embossed backing material in accordance with the present invention.

Referring to FIG. 4, a further embodiment of an embossed pattern 40 is shown. The embossed pattern 40 includes a plurality of depression 42 that are in the shape of a "+" symbol and a "–" symbol in an alternating pattern in the cross web direction. Preferably, the same symbol is aligned in the down web direction. Separating each depression 42 is a land space 44 in both a down web direction 43 and a cross web direction 45. In FIG. 4, the "+" symbol in the embossed pattern 40 has the following dimensions: a total height and width of about 0.91 mm, wherein each of the segments in the "+" have a thickness of about 0.20 mm in both the down web and cross web directions. The "–" symbol in the embossed pattern 40 has the following dimensions: a longest dimension of about 0.91 mm and a shortest dimension of about 0.20 mm. Additionally, the land space between each depression in the down web direction and the cross web direction is about 0.36 mm. Together, this embossed pattern 40 results in a total patterned area of about 16.0% of the total area of the material/tape backing.

Figure 5:
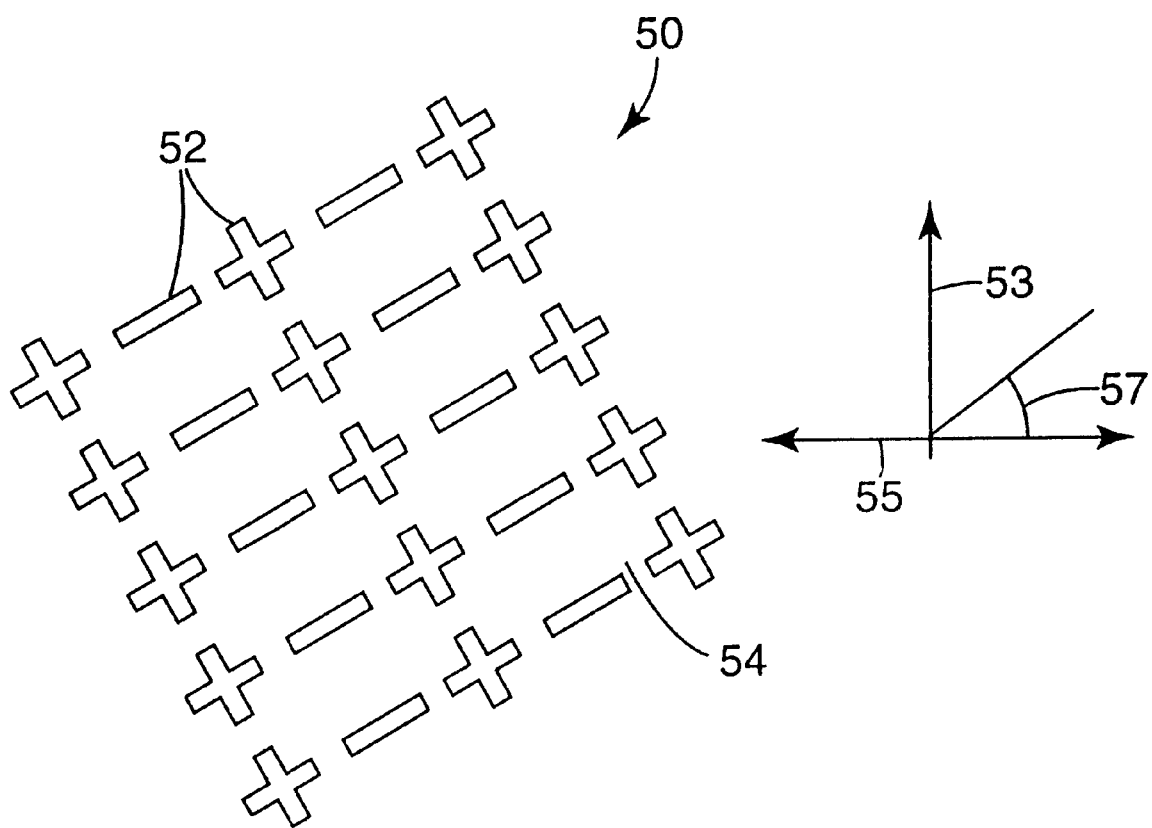
FIG. 5 is a schematic diagram of another embodiment of an embossed backing material in accordance with the present invention.

Referring to FIG. 5, yet a further embodiment of an embossed pattern is shown. This embossed pattern 50 is a similar pattern as depicted in FIG. 4, such that the pattern is a combination of "+" and "–" depressions 52 separated by land areas 54, each with the dimensions as described above in connection with FIG. 4. However, the embossed pattern 50 has been rotated at an angle 57 of about 30° from the cross direction 55. Although shown as a 30° rotation, any pattern can be rotated at any angle less than about 90° from the cross web direction.

In accordance with the present invention, the fibrous web is preferably calendered using a smooth roll that is nipped against another smooth roll. Thus, in a preferred embodiment, the fibrous webs according to the present invention are thermally calendered with a smooth roll and a solid back-up roll (e.g., a metal, rubber, or cotton cloth covered metal) in addition to pattern embossing, described above. During calendering, it is important to closely control the temperature and the pressure of the smooth rolls. In general, the fibers are thermally fused at the points of contact without imparting undesirable characteristics to the fibrous web, such as unacceptable stiffness and/or poor overtaping. In this regard, it is preferred to maintain the temperature of the smooth roll between about 70° C. and 220° C., more preferably between about 85° C. and 180° C. In addition, the smooth roll should contact the fibrous web at a pressure of from about 10 N/mm to about 90 N/mm, more preferably from about 20 N/mm to about 50 N/mm.

While not wishing to be bound by any particular theory, it is believed that smooth roll calendering further adds to the tensile strength of the fibrous web and enhances a variety of material/tape backing properties, including overtaping. In the medical tape environment, a variety of factors are of concern, such as adherence of the tape to its backside (also referred to herein as "overtaping"), curling of the tape edges after application of the tape to the skin (a function of conformability), and the like. It was surprisingly found that tape backings that were made from a method that included a smooth roll calendering step exhibited very straight separation in both the down web and cross web directions when torn and increased overtaping performance.

As mentioned above, the fibrous web is preferably applied with a binding agent, also referred to herein as "resin bonding." In accordance with the present invention, a wide variety of chemical binding agents can be applied to the fibrous webs by art-recognized processes. Nonlimiting examples of useful chemical binding agents include acrylics, vinyl acrylics, acetate/ethylene, polyvinyl acetate, polyurethane, and the like. Whatever chemical binder is employed, it should have an affinity for, and readily bind with, the tensilized nonfracturable staple fibers and/or binder fibers comprising the fibrous web.

It is preferable that the chemical binding agent comprise a water-based chemical binder, including, without limitation, latexes incorporating acrylics, styrene/butadiene rubbers, vinyl acetate/ethylenes, vinyl acetate/acrylates, polyvinyl chloride, polyvinyl alcohols, polyurethanes, vinyl acetates, acrylic/vinyl acetate, a styrene/acrylic and the like. These water-based chemical binders are typically applied to the fibrous web at about 20% to about 50% solids, using any suitable coating method, including, wire-wound rod, reverse roll, air knife, direct and offset gravure, trailing blade, print bond, foam, and spray coating methods.

Specific examples of chemical binding agents according to the present invention, include, without limitation, those available under the trade designations RHOPLEX E-3636 and E-3522 (each an approximately 50% solids styrene/acrylic latex binder), RHOPLEX E-2559 (an approximately 52% solids acrylic latex binder), all from Rohm & Haas Co., Philadelphia, Pa.), type 4402 (an approximately 50% solids styrene/butadiene rubber latex; Mallard Creek Polymers, Charlotte, N.C.), and National Starch No. 78-6283 (an approximately 45% solids acrylic/vinyl acetate copolymer latex; National Starch Corp., Bridgewater, N.J.), with National Starch. No. 78-6283.

The chemical binding agent is applied in amounts sufficient to provide the desirable properties, such as tensile strength and tear properties, demonstrated by the nonwoven sheet materials and tapes of the present invention. However, the amount of chemical binding agent employed can be varied depending upon the intended use. For example, more chemical binding agent may be applied to increase the strength of the nonwoven sheet materials, while less binder may be used to lower the Hand (i.e., improve conformability) of the materials.

In general, when the fibrous web is saturated with a chemical binding agent to form the nonwoven sheet materials and tapes of the present invention, the weight of the chemical binding agent in the fibrous web, after being dried, is from about 10 $g/m^2$ to about 50 $g/m^2$, preferably from about 15 $g/m^2$ to about 40 $g/m^2$. In this regard, it is preferred that the weight ratio of the fibers comprising the fibrous web to the chemical binding agent incorporated in the fibrous web be from about 5:1 to about 1:5, more preferably from about 3:1 to about 1:3, and most preferably from about 2:1 to 1:2.

As mentioned above, a method for producing a material/tape backing in accordance with the present invention includes the following steps: resin bonding a fibrous web, pattern embossing, and smooth roll calendering. In one embodiment, a preferred order of these steps includes: pattern embossing, smooth roll calendering, and resin bonding. In yet another embodiment of the present invention, the smooth roll calendering step is performed first. Then, either pattern embossing step or the resin bonding follows the smooth roll calendering step. Surprisingly, it was found that these preferred sequence of steps results in material/tape backing that improves tensile strength and overtaping without sacrificing a straight cross web and down web tear. For example, it was surprisingly found that these properties were all improved using one of the above sequence of steps as compared to a method including the following sequence: pattern embossing, resin bonding, and smooth roll calendering, or as compared to a method that includes pattern embossing and resin bonding alone.

The fibrous web according to the present invention can also optionally incorporate a water-based release coating, such as a low-adhesion backsize (LAB), at essentially the same time as, or after incorporation of, the chemical binding agent into the web. Preferred useable LABs comprise those listed in, and applied by the methods described in, U.S. Pat. No. 4,973,513. After the chemical binding agent, and optional LAB, is applied, the fibrous web is dried using any appropriate drying means, such as contact drying, circulating air ovens, impingement ovens, through-air ovens, and the like.

Tapes

After the fibrous web has been resin bonded, smooth roll calendered, and pattern embossed to form the nonwoven sheet materials of the present invention, the sheet materials may be wound in a roll for transportation, or made into multilayer laminates for later application of an adhesive, or other appropriate coatings used to form tapes, such as standard medical tapes, masking tapes, and the like. Alternatively, the nonwoven sheet material may be conveyed directly to an adhesive coater, followed by slitting into individual tape rolls.

Preferably, the nonwoven sheet materials are coated with a layer of pressure-sensitive adhesive to form the tapes according to the present invention. In this regard, the pressure-sensitive adhesive that is applied to the nonwoven sheet materials may be solvent-based, water-based, or a hot-melt adhesive. Suitable adhesives, and their methods of application, are described, for example, in U.S. Pat. No. 2,708,192 (phenolic cured rubber based adhesives), U.S. Pat. No. Re. 24,906 (water-based and solvent-based adhesives), and U.S. Pat. No. 4,833,179 (hot-melt adhesives).

In one embodiment, the nonwoven sheet materials of the present invention are coated with a high-solids latex pressure-sensitive adhesive that is moisture insensitive, while also displaying an excellent balance of adhesive properties, such as high compliance, and high shear, without adhesive build. See, e.g., U.S. Pat. Nos. 5,521,229 and 5,624,973 both to Lu et al., and EP Pat. No. 554 832 B to Crandall, et al. for general methods of preparing these types of adhesives. The characteristics and advantages of the preferred pressure-sensitive adhesive derive, at least in part, from the presence of a polymerizable surfactant and a low molecular weight hydrophobic polymer in the latex formulation.

The preferred latex pressure-sensitive adhesives coated on the nonwoven sheet materials of the present invention are produced by emulsifying a mixture of water, acrylate and vinyl monomers, ionic copolymerizable surfactant, optional chain transfer agent, optional crosslinker, and hydrophobic polymer. The emulsion is heated with agitation under nitrogen atmosphere, then treated with initiator in portions to maintain temperature control. The reaction mixture is heated and agitated until reaction is complete. The resulting acrylic latex can then be coated according to a variety of conventional methods known by those skilled in the art.

The acrylate monomer component of the latex pressure-sensitive adhesive preferably comprises $C_4$ to $C_{12}$ alkyl ester acrylate monomers. Suitable alkyl ester acrylate monomers include, without limitation, n-butyl acrylate, amyl acrylate, hexyl acrylate, isooctyl acrylate, 2-ethylhexyl acrylate, isononyl acrylate, decyl acrylate, dodecyl acrylate, and mixtures thereof.

Furthermore, the vinyl monomers combined with the acrylate monomers preferably comprises 1) vinyl esters including but not limited to vinyl acetate, vinyl propionate, vinyl butyrate, and the like, 2) $C_1$ to $C_4$ alkyl esters of (meth)acrylic acid (including but not limited to methyl methacrylate, methyl acrylate, ethyl acrylate, ethyl methacrylate, isobutyl methacrylate, and the like), 3) styrene, and mixtures thereof.

Useful copolymerized hydrophilic acidic monomers include, but are not limited to, those selected from ethylenically unsaturated carboxylic acids, ethylenically unsaturated sulfonic acids, ethylenically unsaturated phosphonic acids, and mixtures thereof. Examples of such compounds include, but are not limited to, acrylic acid, methacrylic acid, itaconic acid, fumaric acid, crotonic acid, citraconic acid, maleic acid, β-carboxyethyl acrylate, 2-sulfoethyl methacrylate, styrene sulfonic acid, 2-acrylamido-2-methylpropane sulfonic acid, vinyl phosphonic acid, and the like. Various combinations of these monomers can be used if desired. Due to their availability and effectiveness in reinforcing (meth)acrylate pressure sensitive adhesives, preferred hydrophilic acidic monomers are the ethylenically unsaturated carboxylic acids, most preferably, acrylic acid.

Examples of useful copolymerizable ionic surfactants in the preferred latex pressure-sensitive adhesive include, but are not limited to, those described in WO 89/12618. The surfactants described therein have a hydrophobic portion containing alpha-beta ethylenic unsaturation, a hydrophilic portion containing a poly(alkyleneoxy)segment, and an ionic segment. The preferred copolymerizable surfactant is MAZON SAM-211 surfactant (PPG Industries, Inc.; described as an ethylene polyalkoxy ammonium sulfate, wherein the number of alkoxy groups is between about 5 and about 25, with a typical example having about 15 to about 20 ethoxy groups).

The latex pressure-sensitive adhesive may optionally further comprise a crosslinking agent, including, without limitation, multifunctional acrylates such as diacrylates, triacrylates, and tetraacrylates, such as 1,6-hexanedioldiacrylate, poly(ethylene glycol)diacrylates, poly (butadine)diacrylates, polyurethane diacrylates, and trimethylolpropane triacrylate; 4-acryloxybenzophenone; divinyl benzene; and mixtures thereof. Also, optional chain transfer agents, such as carbon tetrabromide, mercaptans, alcohols, and mixtures thereof may be included.

As noted above, the preferred latex pressure-sensitive adhesive includes a low molecular weight hydrophobic polymer. The term "hydrophobic polymer", as used herein, refers to a water insoluble polymer. Useful hydrophobic polymers have an average molecular weight ranging from about 400 to about 50,000, preferably about 500 to about 20,000, most preferably about 600 to about 10,000. Examples of useful low molecular weight noncopolymerizable hydrophobic polymers include, but are not limited to, those selected from the group consisting of polystyrene resins such as PICCOLASTIC A75, D125, and D150 available from Hercules Chemicals; poly(methylmethacrylate) (PMMA) resin; polybutadiene; poly(alpha-methylstyrene); butadiene-styrene block copolymers; and rosin esters such as FORAL 85 and 105, available from Hercules, and mixtures thereof.

Preferably, the adhesive coated tapes of the present invention also utilize a releasable liner that covers the adhesive layer, or a release coating, such as a low adhesion backsize (LAB), coated on the nonadhesive side of the tape, to facilitate the winding of the tape into easy to use rolls. Preferably, an LAB coating is applied to the nonadhesive side of the tape using conventional coating methods in the textile industry.

It is preferred that the LAB comprise a water-based composition, however, solvent-based materials such as polyvinylcarbamate are also useful. Suitable components of the water-based LAB include, without limitation, polyethylenes, fluorochemicals, acrylates, silicones, vinyl copolymers, and combinations of these polymers with other polymers. For example, acceptable LABs useful in the tapes of the present invention are described in U.S. Pat. Nos. 4,728,571 and in 4,973,513, a water-based LAB.

Applicants have surprisingly invented nonwoven sheet materials, and tapes formed therefrom, comprised of essentially nonfracturable fibers that can be made readily tearable (i.e., fracturable) in the cross web direction of the sheet or tape, and yet are conformable in use. In addition, these materials and tapes can also exhibit a number of other advantageous properties including, enhanced tensile strength, tearability, enhanced overtaping, and a uniformity of strength in both the down web direction and cross web direction.

Typically, nonwoven sheet materials or tapes must sacrifice certain properties in favor of others. For example, to obtain a tape that is tearable in the cross web direction (e.g., a category I tape), overall tape strength, and in particular, must be compromised. Likewise, to obtain a tape with good tensile strength (e.g., a category II tape), tearability, and often conformability, are lost. Thus, category I and II tapes are often limited in their application. Conversely, the nonwoven sheet materials and tapes of the present invention should find wide use throughout the health-care field, and anywhere else, where a strong, conformable, and readily tearable tape is required. Specifically, the nonwoven sheet materials and tapes of the present invention combine the down web and cross web direction tensile strength advantages of typical category II materials with the Hand (i.e., conformability) and down and cross web direction tear advantages of typical category I materials to provide materials with wide applicability in the health-care field, athletics, and other areas.

The particular tear characteristics of a nonwoven sheet material or tape of the present invention is evaluated according to the test procedures detailed below in the Examples section.

EXAMPLES

This invention is further illustrated by the following examples that are not intended to limit the scope of the invention. In the examples, all parts, ratios and percentages are by weight unless otherwise indicated.

Test Protocols

Tensile Strength

ASTM Test Method No. D3759-83 was performed using a meter commercially available under the trade designation THWING-ALBERT TESTER Model EJA/2000, from Thwing-Albert Company, Philadelphia, Pa., a sample width of 2.54 cm, a gauge length of 12.7 cm, and a crosshead speed of 12.7 cm/min. Reported for each sample tested is the maximum force applied to the test sample to obtain the tensile value at point of break.

Hand

The total Hand measurement in grams of a nonwoven sheet material sample provides a measure of the drape/conformability of the sample. Those materials with a relatively high Hand value are stiff and nonconformable. Conversely, relatively low Hand values reflect soft conformable materials. The Hand values reported for the samples of this invention were obtained on a THWING-ALBERT HANDLE-O-METER Model No. 211-300 (Thwing-Albert Instrument Co., Philadelphia, Pa.), according to the procedures outlined in the instruction manual included with Model No. 211-300. All of the Hand measurements were performed on about 20-cm square sheet materials.

Overtaping

A "bottom" series of 5.08-cm×25.4-cm adhesive tape strips was adhered to a clean Plexiglas horizontal platform by rolling the strips, adhesive side down, back and forth once with a 10-kg roller. A "top" series of 2.54-cm and 25.4-cm adhesive tape strips (taken from the same lot of samples as the "bottom" series) was placed, adhesive side down, on top of the "bottom" series of tape strips. The top strips were centered side-to-side across the bottom strips width and extended 2.54 cm beyond the bottom strips. A 3 gram weight was then attached to each of the extended ends of the top strips and the strips were rolled once back and forth with the roller. The weighted ends of each top tape strip was pulled down until the lines of peel from the backsides of the bottom tape strips reached a zero mark on the Plexiglas platform. The platform was then moved to a room having a constant temperature and humidity of 40° C./75% relative humidity, respectively, and positioned upright 20 degrees from vertical so that the weights hung freely. After one hour, the distance that a "top" tape strip peeled from an anchored "bottom" tape strip was recorded as the "overtaping" value for that adhesive tape sample.

Tear

Cross Direction Tear Test

A 7.6-cm (cross direction) by 10.2-cm (machine direction) sample of backing or tape was held at the center of the 10.2-cm length with the thumb and index finger of each hand spaced no more than 1.3 cm apart. The sample was then torn by moving one's hands in opposite directions from one another and perpendicular to the cross direction plane of the sample until the tear had propagated through the end of the sample. The rate of tear propagation was believed to be about 7.6 cm per second. A metric ruler was used to measure (in millimeters) the maximum distance that the tear deviated from a straight line.

Machine Direction Tear Test

A 7.6-cm (cross direction) by 30.5-cm (machine direction) sample of backing or tape was held at the center of the 7.6-cm length with the thumb and index finger of each hand spaced no more than 1.3 cm apart. The sample was then torn by moving one's hands in opposite directions from one another and perpendicular to the machine direction plane of the sample until the tear had propagated through the end of the sample. The rate of tear propagation was believed to be about 7.6 cm per second. A metric ruler was used to measure (in millimeters) the maximum distance that the tear deviated from a straight line.

Carded Nonwoven Web (Web A)

A carded nonwoven web utilized as a starting material in the following examples was made on a machine commercially available under the trade designation of HERGETH RANDOM-CARD, from Hergeth-Hollingsworth, GMBH, Dülman, Germany, utilizing conventional nonwoven web formation techniques. The fiber blend included:

60% polyethylene terephthalate (PET) staple fiber (0.95 denier×3.8 cm, L-70, Hoechst Celanese Corp., Spartanburg, S.C.), 20% rayon staple fiber (1.5 denier×4.0 cm, Merge 8649, Lenzing, Charlotte, N.C.), and 20% bicomponent PET thermal bonding fiber (2.0 denier×3.8 cm, T-254, Hoechst Celanese Corp., Spartanburg, S.C.).

The resulting carded nonwoven web had a fiber basis weight of 30 g/m$^2$ and is referred to as "Web A" in the following examples.

Carded Nonwoven Web (Web B)

Another carded nonwoven web utilized as a starting material in the following examples was made on a Hergeth Random-Card machine (Hergeth-Hollingsworth, GMBH, Dülman, Germany) utilizing conventional nonwoven web formation techniques. The fiber blend consisted of:

60% polyethylene terephthalate (PET) staple fiber (0.95 denier×3.8 cm, L-70, Hoechst Celanese Corp., Spartanburg, S.C.), 20% polypropylene staple fiber (2.2 denier×4.0 cm, Hercules T-196, Wilmington, Del.), and 20% bicomponent PET thermal bonding fiber (2.0 denier×3.8 cm, T-254, Hoechst Celanese Corp., Spartanburg, S.C.).

The resulting carded nonwoven web had a fiber basis weight of 30 g/m$^2$ and is referred to as "Web B" in the following examples.

Carded Nonwoven Web (Web C)

Another carded nonwoven web utilized as a starting material in the following examples was made on a machine commercially available under the trade designation of HERGETH RANDOM-CARD, from Hergeth-Hollingsworth, GMBH, Dülman, Germany, utilizing conventional nonwoven web formation techniques. The fiber blend included:

78% polyethylene terephthalate (PET) staple fiber (1.0 denier×3.8 cm, T-121, Hoechst Celanese Corp., Spartanburg, S.C.), and 22% bicomponent PET thermal bonding fiber (2.0 denier×5.1 cm, K-52, Konamatsu The resulting carded nonwoven web had a fiber basis weight of 23 g/m$^2$ and is referred to as "Web C" in the following examples.

Comparative Example A
(Process Sequence PR, Engraved Pattern A)

Comparative Example A (C.A) was prepared by using the nonwoven carded Web A that was conveyed at a speed of about 12.2 m/min to a two-roll heated calender station (manufactured by Energy Solutions Inc., St. Paul, Minn.) and pattern embossed (Process Step-P) using the process conditions listed in Table 1. The calender station was set-up with a 25.4-cm diameter×55.9-cm wide smooth steel roll in the lower position and a 25.4-cm diameter×55.9-cm wide steel roll with an engraved pattern (Pattern A) in the upper position. The engraved Pattern A (pattern 60 shown in FIG. 6) had an 11.5% bond area and consisted of 0.914-mm (cross-direction 65)×0.203-mm (machine-direction 63) rectangular-shaped depressions 62 spaced 0.356 mm apart in the cross-direction and 1.067 mm apart in the machine-direction.

The pattern-embossed web was subsequently resin bonded (Process Step-R) with a 37.5% solids acrylic vinyl acetate copolymer latex (Product No. 78-6283, National Starch, Bridgewater, N.J.; 45% solids diluted with tap water) containing 1% antifoam agent (Antifoam B Silicone Emulsion, Dow Corning, Midland, Mich.) by passing through a gravure coating station at a speed of about 12.1 m/min and a nip pressure of about 0.41 N/mm. The gravure coater was set-up with a 20.3-cm diameter×61-cm wide threaded rubber roll in the upper position and a 20.3-cm diameter×61-cm wide, 16 lines/cm trihelical pattern steel roll (Northern Engraving, Green Bay, Wis.) in the lower position. The resulting nonwoven sheet material was dried by passing through a 188° C. oven at a speed of about 12.3 m/min and collected on a 7.62-cm cardboard core.

Comparative Example B
(Process Sequence PRS, Engraved Pattern A)

The nonwoven carded Web A was pattern embossed and resin bonded as described in Comparative Example A using the pattern embossing conditions listed in Table 1. The dried nonwoven sheet material was then smooth-roll calendered (Process Step-S) using the process conditions listed in Table 1. The smooth-roll calendering process step was accomplished similarly to the pattern embossing step described in Comparative Example A, except that the calender station was set-up with a smooth steel roll having a cotton cloth covering in place of the engraved roll in the upper position. The resulting nonwoven sheet material was collected on a 7.62-cm cardboard core.

EXAMPLES 1 AND 2
(Process Sequence PSR, Engraved Pattern A)

The nonwoven carded Web A was pattern embossed as described in Comparative Example A using the process conditions listed in Table 1, and subsequently smooth-roll calendered as described in Comparative Example B using the process conditions listed in Table 1. The resulting nonwoven sheet material was then resin bonded, dried in an oven and collected on a 7.62-cm cardboard core as described in Comparative Example A. Another nonwoven sheet material was prepared in the same manner and designated Example 2.

EXAMPLE 3
(Process Sequence SPR, Engraved Pattern A)

The nonwoven carded Web A was smooth-roll calendered as described in Comparative Example B using the process conditions listed in Table 1, and subsequently pattern embossed as described in Comparative Example A using the process conditions listed in Table 1. The resulting nonwoven sheet material was then resin bonded, dried in an oven and collected on a 7.62-cm cardboard core as described in Comparative Example B.

EXAMPLE 4
(Process Sequence SRP, Engraved Pattern A)

The nonwoven carded Web A was smooth-roll calendered as described in Comparative Example B using the process conditions listed in Table 1, and subsequently resin bonded and dried in an oven as described in Comparative Example A. The resulting nonwoven sheet material was then pattern embossed as described in Comparative Example A using the process conditions listed in Table 1 and collected on a 7.62-cm cardboard core.

Comparative Example C
(Process Sequence PR, Engraved Pattern A)

Comparative Example C (C.C) was prepared using the nonwoven carded Web A that was pattern embossed and resin bonded as described in Comparative Example A using the pattern embossing conditions listed in Table 1. The resulting nonwoven sheet material was collected on a 7.62-cm cardboard core.

Comparative Example D
(Process Sequence PR, Engraved Pattern B)

Figure 7:
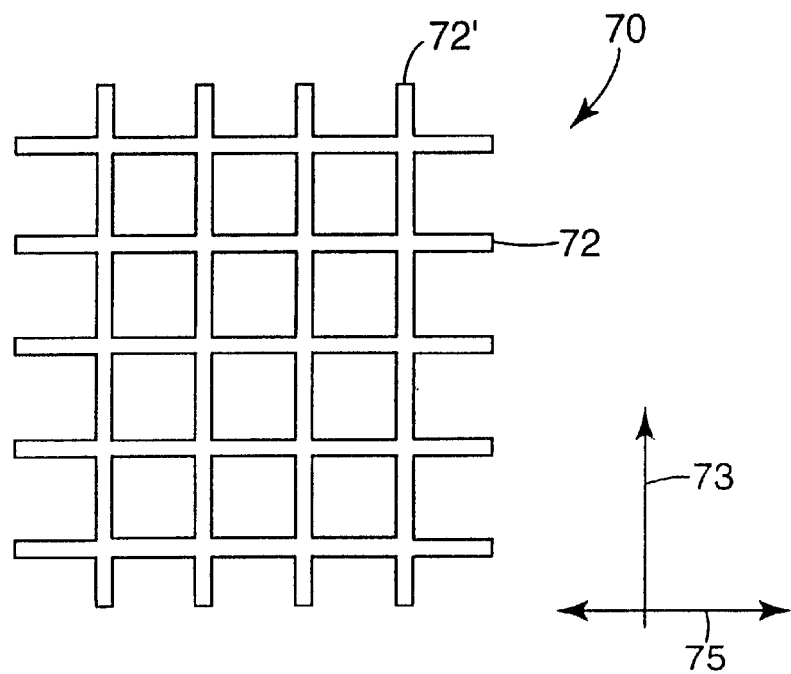
FIG. 7 is a schematic diagram of an embossed backing material including a series of intersecting continuous lines along both the cross web and down web directions of the material.

Comparative Example D (C.D) was prepared by using the nonwoven carded Web C that was pattern embossed and resin bonded as described in Comparative Example A using the pattern embossing conditions listed in Table 1, except that engraved Pattern B (pattern 70 shown in FIG. 7) was used in place of engraved Pattern A. Engraved Pattern B had a 29.4% bond area and consisted of a series of raised continuous line elements 72 and 72' that ran at right angles to each other in the cross-direction 75 and machine-direction 73, respectively. This so-called "box pattern" is described in U. S. Pat. No. 5,496,603 (Riedel, et al.). The resulting nonwoven sheet material was collected on a 7.62-cm cardboard core.

Comparative Example E
(Process Sequence PRS, Engraved Pattern A)

The nonwoven carded Web A was pattern embossed, resin bonded, and smooth-roll calendered as described in Comparative Example B using the process conditions listed in Table 1, except that the cotton cloth covering the smooth steel roll was replaced by a material made of rubber. The resulting nonwoven sheet material was dried in an oven and collected on a 7.62-cm cardboard core.

EXAMPLE 5
(Process Sequence PSR, Engraved Pattern A)

The nonwoven carded Web A was pattern embossed, smooth-roll calendered, and resin bonded as described in Example 2 using the process conditions listed in Table 1, except that the cotton cloth covering the smooth steel roll was replaced by a material made of rubber. The resulting nonwoven sheet material was dried in an oven and collected on a 7.62-cm cardboard core.

EXAMPLE 6
(Process Sequence SPR, Engraved Pattern A)

The nonwoven carded Web A was smooth-roll calendered, pattern embossed, and resin bonded as described in Example 3 using the process conditions listed in Table 1, except that the cotton cloth covering the smooth steel roll was replaced by a material made of rubber. The resulting nonwoven sheet material was dried in an oven and collected on a 7.62-cm cardboard core.

EXAMPLE 7
(Process Sequence SRP, Engraved Pattern A)

The nonwoven carded Web A was smooth-roll calendered, pattern embossed, and resin bonded as described in Example 4 using the process conditions listed in Table 1, except that the cotton cloth covering the smooth steel roll was replaced by a material made of rubber. The resulting nonwoven sheet material was dried in an oven and collected on a 7.62-cm cardboard core.

EXAMPLE 8
(Process Sequence SPR, Engraved Pattern C)

The nonwoven carded Web A was smooth-roll calendered, pattern embossed, and resin bonded as described in Example 3 using the process conditions listed in Table 1, except that engraved pattern C (shown in FIG. 2, described above) was used in place of engraved Pattern A, and that the cotton cloth covering the smooth steel roll was replaced by a material made of rubber. The engraved Pattern C had an 18.6% bond area and consisted of rectangular-shaped depressions that were aligned in both the cross-direction and the machine-direction. The resulting nonwoven sheet material was dried in an oven and collected on a 7.62-cm cardboard core.

EXAMPLE 9
(Process Sequence SPR, Engraved Pattern D)

The nonwoven carded Web A was smooth-roll calendered, pattern embossed, and resin bonded as described in Example 3 using the process conditions listed in Table 1, except that engraved pattern D (shown in FIG. 3, described above) was used in place of engraved Pattern A, and that the cotton cloth covering the smooth steel roll was replaced by a material made of rubber. The engraved Pattern D had a 20.5% bond area and consisted of plus-shaped depressions that were aligned in cross-direction rows and machine-direction columns. The resulting nonwoven sheet material was dried in an oven and collected on a 7.62-cm cardboard core.

EXAMPLE 10
(Process Sequence SPR, Engraved Pattern E)

The nonwoven carded Web A was smooth-roll calendered, pattern embossed, and resin bonded as described in Example 3 using the process conditions listed in Table 1, except that engraved pattern E (shown in FIG. 1, described above) was used in place of engraved Pattern A. The engraved Pattern E had a 15.4% bond area and consisted of elongated cross-shaped depressions that were aligned in cross-direction rows and machine-direction columns. The resulting nonwoven sheet material was dried in an oven and collected on a 7.62-cm cardboard core.

EXAMPLE 11
(Process Sequence SPR, Engraved Pattern F)

The nonwoven carded Web A was smooth-roll calendered, pattern embossed, and resin bonded as described in Example 3 using the process conditions listed in Table 1, except that engraved pattern F (shown in FIG. 4, described above) was used in place of engraved Pattern A, and that the cotton cloth covering the smooth steel roll was replaced by a material made of rubber. The engraved Pattern F had a 16.0% bond area and consisted of alternating rectangular-shaped and plus-shaped depressions that were aligned in cross-direction rows and machine-direction columns. The resulting nonwoven sheet material was dried in an oven and collected on a 7.62-cm cardboard core.

EXAMPLE 12
(Process Sequence SRP, Engraved Pattern F)

The nonwoven carded Web A was smooth-roll calendered, resin bonded, and pattern embossed as described in Example 4 using the process conditions listed in Table 1, except that engraved pattern F (as described in Example 12 and shown in FIG. 4) was used in place of engraved Pattern A, and that the cotton cloth covering the smooth steel roll was replaced by a material made of rubber. Also, the acrylic vinyl acetate copolymer latex binder (Product No. 78-6283) was replaced by an acrylic styrene copolymer latex binder (Product No. E-3636, Rohm & Haas, Philadelphia, Pa.; 50% solids diluted with water). The resulting nonwoven sheet material was dried in an oven and collected on a 7.62-cm cardboard core.

TABLE 1

Fiber Weight, Chemical Binder Weight, Pattern Embossing Conditions, And Smooth-Roll Calendering Conditions for Nonwoven Sheet Materials of Comparative Examples A–E and Examples 1–12

| Ex. | Process Sequence | Pattern | Fiber Weight (g/m$^2$) | Binder Weight (g/m$^2$) | Pattern Embossing Conditions[1] (° C. - N/mm - m/min) | Smooth Roll Calender Conditions[2] (° C. - N/mm - m/min) |
| --- | --- | --- | --- | --- | --- | --- |
| C.A | PR | A | 30 | 30 | 157 - 67.4 - 12.80 | Not Applicable |
| C.B | PRS | A | 30 | 30 | 154 - 67.4 - 12.50 | 156 - 43.1 - 12.80 |
| 1 and 2 | PSR | A | 30 | 30 | 160 - 67.4 - 12.65 | 156 - 43.1 - 12.80 |
| 3 | SPR | A | 30 | 30 | 157 - 67.4 - 12.80 | 155 - 43.1 - 12.80 |
| 4 | SRP | A | 30 | 30 | 159 - 67.4 - 12.80 | 155 - 43.1 - 12.80 |
| C.C | PR | A | 30 | 30 | 154 - 67.4 - 9.0 | Not Applicable |
| C.D | PR | B | 23 | 15 | 222 - 38.5 - 20.8 | Not Applicable |
| C.E | PRS | A | 30 | 30 | 154 - 67.4 - 9.0 | 154 - 49.9 - 9.0 |
| 5 | PSR | A | 30 | 30 | 154 - 67.4 - 9.1 | 154 - 49.9 - 9.1 |
| 6 | SPR | A | 30 | 30 | 152 - 67.4 - 9.9 | 154 - 49.9 - 9.9 |
| 7 | SRP | A | 30 | 30 | 153 - 67.4 - 9.6 | 154 - 49.9 - 9.6 |
| 8 | SPR | C | 30 | 30 | 156 - 140.1 - 9.1 | 154 - 49.9 - 9.1 |

TABLE 1-continued

Fiber Weight, Chemical Binder Weight, Pattern Embossing Conditions,
And Smooth-Roll Calendering Conditions for Nonwoven Sheet Materials
of Comparative Examples A–E and Examples 1–12

| Ex. | Process Sequence | Pattern | Fiber Weight $(g/m^2)$ | Binder Weight $(g/m^2)$ | Pattern Embossing Conditions[1] (° C. - N/mm - m/min) | Smooth Roll Calender Conditions[2] (° C. - N/mm - m/min) |
|---|---|---|---|---|---|---|
| 9 | SPR | D | 30 | 30 | 156 - 140.1 - 9.1 | 154 - 49.9 - 9.1 |
| 10 | SPR | E | 30 | 30 | 149 - 70.1 - 6.1 | 154 - 49.9 - 6.1 |
| 11 | SPR | F | 30 | 30 | 156 - 116.5 - 9.1 | 154 - 49.9 - 9.1 |
| 12 | SRP | F | 30 | 30 | 156 - 116.5 - 9.1 | 154 - 49.9 - 9.1 |

[1]Pattern Embossing Nip Diameter was 25.4 cm (except 40.6 cm for Ex. C.D and 22.9 cm for Ex. 10).
[2]Smooth Roll Calender Nip Diameter was 25.4 cm.

Comparative Examples F and G and

EXAMPLES 13–16

Adhesive Tapes

The nonwoven sheet materials described in Comparative Examples A and B and in Examples 1–4 were converted into the adhesive tapes of Comparative Example F and G and of Examples 13–16, respectively. The nonwoven sheet materials were coated on the smooth side with 28 g/m² of an emulsion pressure sensitive adhesive (PSA) comprised of polymeric isooctyl acrylate/vinyl acetate/acrylic acid/D-125 polystyrene resin (Hercules Chemicals)) (89/6/3/2), the preparation of which is generally described in EP Pat. No. 554 832 B. The pattern embossed side of the sheet materials was coated with 2 g/m² of a urethane low-adhesion backside (LAB) comprised of the reaction product of polyvinyl alcohol and octadecyl isocyanate (as described in U.S. Pat. No. 3,121,021).

Evaluations

EXAMPLES 1–4 and

Comparative Examples A and B

The nonwoven sheet materials described in Comparative Examples A and B and in Examples 1–4 were cut into appropriate sample sizes and evaluated (machine direction and cross-direction) for Tensile Strength at break and for Hand. The results are shown in Table 2. All nonwoven sheet samples of these examples were observed to be hand-tearable and to provide a clean, straight tear in the cross web direction and the down web direction with minimal fraying.

TABLE 2

Evaluation Results for Nonwoven Sheet Materials of Comparative Examples A and B, and Examples 1–4

| | | | Tensile Strength MD (N/cm) | | | Tensile Strength CD (N/cm) | | | Hand (MD) (g/20 cm × 20 cm) | | | Hand (CD) (g/20 cm × 20 cm) | | |
|---|---|---|---|---|---|---|---|---|---|---|---|---|---|---|
| Ex. | Process Sequence | Pattern | N | Avg. | SD | N | Avg. | SD | N | Avg. | SD | N | Avg. | SD |
| C.A | PR | A | 9 | 11.4 | 0.5 | 3 | 7.5 | 0.1 | 6 | 107 | 8 | 6 | 76 | 8 |
| C.B | PRS | A | 9 | 8.4 | 0.2 | 3 | 5.2 | 0.1 | 6 | 45 | 5 | 6 | 130 | 0 |
| 1 | PSR | A | 9 | 11.9 | 0.7 | 3 | 7.9 | 0.1 | 6 | 67 | 3 | 6 | 48 | 3 |
| 2 | PSR | A | 9 | 13.0 | 0.6 | 3 | 9.1 | 0.2 | 6 | 69 | 8 | 6 | 64 | 8 |
| 3 | SPR | A | 9 | 11.9 | 0.2 | 3 | 8.4 | 0.2 | 6 | 90 | 7 | 6 | 62 | 7 |
| 4 | SRP | A | 9 | 15.6 | 0.7 | 3 | 8.2 | 0.8 | 6 | 72 | 2 | 6 | 44 | 2 |

EXAMPLES 5–12 and

Comparative Examples C, D and E

The nonwoven sheet materials described in Comparative Examples C, D and E and in Examples 5–12 were cut into appropriate sample sizes and evaluated (machine direction and cross-direction) for Tensile Strength at break and for Tear (machine direction and cross-direction). The results are shown in Table 3.

TABLE 3

Evaluation Results for Nonwoven Sheet Materials of Comparative Examples C, D and E, and Examples 5–12

| | Process | | Tensile Strength MD (N/cm) | | | Tensile Strength CD (N/cm) | | | Tear (MD) (mm) | | | Tear (CD) (mm) | | |
|---|---|---|---|---|---|---|---|---|---|---|---|---|---|---|
| Ex. | Sequence | Pattern | N | Avg. | SD | N | Avg. | SD | N | Avg. | SD | N | Avg. | SD |
| C.C | PR | A | 9 | 10.7 | 1.0 | 3 | 8.9 | 0.6 | 3 | 45 | 2 | 3 | 2 | 1 |
| C.D | PR | B | 520 | 16.6 | 1.5 | | | | 3 | 5 | 1 | 3 | 19 | 11 |
| C.E | PRS | A | 9 | 10.6 | 1.3 | 3 | 8.5 | 1.0 | | | | | | |
| 5 | PSR | A | 9 | 11.1 | 1.6 | 3 | 10.7 | 0.4 | | | | | | |
| 6 | SPR | A | 9 | 9.6 | 1.1 | 3 | 9.1 | 0.3 | 3 | 50 | 10 | 3 | 2 | 2 |
| 7 | SRP | A | 9 | 13.5 | 0.7 | 3 | 9.6 | 0.1 | 3 | 34 | 5 | 3 | 2 | 2 |
| 8 | SPR | C | 9 | 11.3 | 0.5 | 3 | 6.7 | 0.5 | 3 | 3 | 3 | 3 | 6 | 4 |
| 9 | SPR | D | 9 | 15.3 | 2.0 | 3 | 7.6 | 0.6 | 3 | 2 | 2 | 3 | 1 | 1 |
| 10 | SPR | E | 9 | 17.5 | 0.8 | 3 | 6.8 | 0.1 | 3 | 2 | 1 | 3 | 39 | 15 |
| 11 | SPR | F | 9 | 11.8 | 1.5 | 3 | 7.3 | 0.4 | 3 | 1 | 2 | 3 | 2 | 2 |
| 12 | SRP | F | 9 | 17.1 | 1.3 | 3 | 8.8 | 0.7 | 3 | 2 | 2 | 3 | 5 | 3 |

*The medical tape QUICKTAPE, 3M, 5 cm wide (as opposed to 7.6 cm tested in other Examples). Thus, the tear results are lower due to the narrower sample size, whereas high tensile strength can be attributed to a significantly lower pattern embossing pressure.

EXAMPLES 13–16 and

Comparative Examples F and G

The adhesive tapes described in Comparative Examples F and G and in Examples 13–16 were cut into appropriate sample sizes and evaluated for overtaping. The results are shown in Table 4. All adhesive tape samples of these examples were observed to be hand-tearable and to provide a clean, straight tear in the cross-direction with minimal fraying.

TABLE 4

Evaluation Results for Adhesive Tapes of Comparative Examples F and G and Examples 13–16

| | NW Sheet Material (Ex.) | Process Sequence | Pattern | Overtaping (mm) | | | |
|---|---|---|---|---|---|---|---|
| Ex. | | | | N | Average | St. Deviation | Fall Off? |
| C.F | C.A | PR | A | 3 | 76 | 0 | Yes |
| C.G | C.B | PRS | A | 3 | 130 | 0 | Yes |
| 13 | 1 | PSR | A | 3 | 1 | 1 | No |
| 14 | 2 | PSR | A | 3 | 2 | 1 | No |
| 15 | 3 | SPR | A | 3 | 10 | 10 | No |
| 16 | 4 | SRP | A | 3 | 3 | 1 | No |

Conclusions

It can be concluded from the test results provided in Tables 2, 3 and 4 that the hand-tearable, nonwoven sheet materials and adhesive tapes of the present invention (all made with resin-bonding, pattern-embossing, and smooth-roll calendering process steps) have improved tensile strength, and/or overtaping properties when compared with corresponding materials made without a smooth-roll calendering process step or with a PRS process sequence (Comparative Examples A–G). For example, as observed from Table 2, the sheet materials made from SRP and PSR process sequences possess the highest tensile strengths. From Table 4 it is observed that the adhesive tapes made from sheet materials using the SRP, SPR, and PSR process sequences all possess superior overtaping properties.

It can be concluded from the test results provided in Table 3 that the engraved pattern can be designed so that the hand-tearable nonwoven sheet materials and adhesive tapes of the present invention will tear very straight in the cross direction, machine direction, or both. In addition, the sequence of bonding steps can be varied to provide improved tensile strength properties when compared with corresponding materials made without a smooth-roll calendering process step (Comparative Examples C and D). For example, comparing the nonwoven sheet materials having an engraved Pattern A (Table 3), the sheet material made with the SRP process sequence possessed the highest tensile strength.

Comparative Example H
(Process Sequence PR, Engraved Pattern G)

The nonwoven carded Web A was conveyed at a speed of about 13 m/min to a two-roll heated calender station (manufactured by Energy Solutions Inc., St. Paul, Minn.) and pattern embossed (Process Step-P) using the process conditions listed in Table 5. The calender station was set-up with a 25.4-cm diameter×55.9-cm wide smooth steel roll in the lower position and a 25.4-cm diameter×55.9-cm wide steel roll with an engraved pattern (Pattern G) in the upper position. The engraved Pattern G is similar to Pattern A (shown in FIG. 6) except that it had a 12% bond area and consisted of 0.8-mm (cross-direction)×0.5-mm (machine-direction) rectangular-shaped depressions spaced 0.5 mm apart in the cross-direction and 1 mm apart in the machine-direction. The pattern-embossed web was subsequently resin bonded (Process Step-R) with a 25% solids acrylic vinyl acetate copolymer latex (Product No. 78-6283, National Starch, Bridgewater, N.J.; 45% solids diluted with deionized water) containing 0.5% antifoam agent (Antifoam B Silicone Emulsion, Dow Corning, Midland, Mich.) and 0.5% surfactant (TRITON GR-5 Union Carbide Corp., Canbury, Conn.) by passing through a gravure coating station at the conditions listed in Table 5. The gravure coater was set-up with a 20.3-cm diameter×61-cm wide threaded rubber roll in the upper position and a 20.3-cm diameter×61-cm wide, 16 lines/cm trihelical pattern steel roll (Northern Engraving, Green Bay, Wis.) in the lower position. The resulting nonwoven sheet material was dried by passing through an oven at conditions listed in Table 5 and collected on a 7.62-cm cardboard core.

EXAMPLE 17
(Process Sequence SPR, Engraved Pattern G)

The nonwoven carded Web A was conveyed at a speed of about 13 m/min to a two-roll heated calender station (manufactured by Energy Solutions Inc., St. Paul, Minn.) and smooth roll calendered (Process Step-S) using the process conditions listed in Table 5. This step was accomplished similarly to the pattern embossing step described in Comparative Example H, except that the calender station was set-up with a smooth steel roll (25.4 cm diameter×55.9 cm wide) in place of the engraved roll in the upper position. The resulting nonwoven sheet material was then pattern embossed and resin bonded as described in Comparative Example F using the pattern embossing conditions listed in Table 5. The resulting nonwoven sheet material was collected on a 7.62-cm cardboard core.

Comparative Example I
(Process Sequence PR, Engraved Pattern A)

Figure 6:
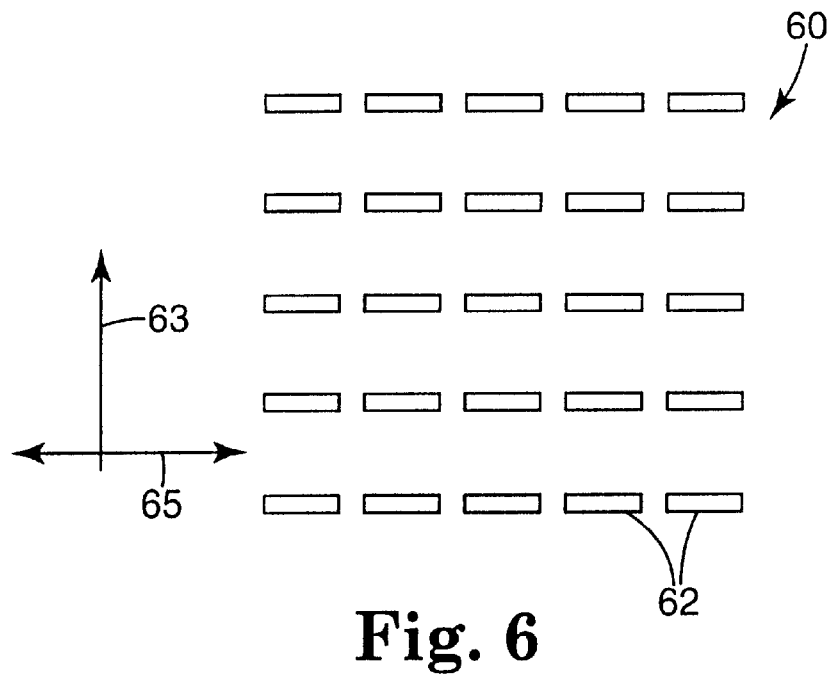
FIG. 6 is a schematic diagram of an embossed backing material including a series of discontinuous lines along a cross web direction of the material.

The nonwoven carded Web B was conveyed at a speed of about 13 m/min to a two-roll heated calender station (manufactured by Energy Solutions Inc., St. Paul, Minn.) and pattern embossed (Process Step-P) using the process conditions listed in Table 5. The calender station was set-up with a 25.4-cm diameter×55.9-cm wide smooth steel roll in the lower position and a 25.4-cm diameter×55.9-cm wide steel roll with an engraved pattern (Pattern A) in the upper position. The engraved Pattern A (as shown in FIG. 6) had an 11.5% bond area and consisted of 0.91-mm (cross-direction)×0.203-mm (machine-direction) rectangular-shaped depressions spaced 0.35 mm apart in the cross-direction and 1.067 mm apart in the machine-direction. The pattern-embossed web was subsequently resin bonded as described in Comparative Example H at the conditions listed in Table 5. The gravure coater was set-up with a 20.3-cm diameter×61-cm wide threaded rubber roll in the upper position and a 20.3-cm diameter×61-cm wide, 16 lines/cm trihelical pattern steel roll (Northern Engraving, Green Bay, Wis.) in the lower position. The resulting nonwoven sheet material was dried by passing through an oven at conditions listed in Table 5 and collected on a 7.62-cm cardboard core.

EXAMPLE 18
(Process Sequence SPR, Engraved Pattern A)

The nonwoven carded Web A was smooth roll calendered as described in Example 17, using the conditions listed in Table 5. This web was subsequently pattern embossed as described in Comparative Example I using the process conditions listed in Table 5. The resulting nonwoven sheet material was collected on a 7.62-cm cardboard core.

EXAMPLE 19
(Process Sequence SPR Engraved Pattern A)

The nonwoven carded Web B was smooth roll calendered as described in Example 17, using the conditions listed in Table 5. This web was subsequently pattern embossed as described in Comparative Example I using conditions listed in Table 5. Then, the calendered embossed sheet was subsequently resin bonded (Process Step-R) with a 25% solids acrylic polymer solution (E-3522, Rohm and Haas Company, Philadelphia, Pa.; 52% solids diluted with deionized water) containing 0.5% antifoam agent (Antifoam B Silicone Emulsion, Dow Corning, Midland, Mich.) and 0.5% surfactant (Triton GR-5 Union Carbide Corp., Canbury, Conn.) by passing through a gravure coating station at the conditions listed in Table 5. The gravure coater was set-up with a 20.3-cm diameter×61-cm wide threaded rubber roll in the upper position and a 20.3-cm diameter× 61-cm wide, 16 lines/cm trihelical pattern steel roll (Northern Engraving, Green Bay, Wis.) in the lower position. The resulting nonwoven sheet material was collected on a 7.62-cm cardboard core.

EXAMPLE 20
(Process Sequence SRP Engraved Pattern A)

The nonwoven carded Web B was smooth roll calendered as described in Example 17, resin bonded as described in Example 19, and subsequently pattern embossed as described in Comparative Example I using conditions listed in Table 5. The resulting nonwoven sheet material was collected on a 7.62-cm cardboard core.

TABLE 5

Fiber Weight, Chemical Binder Weight, Pattern Embossing Conditions, and Smooth-Roll Calendering Conditions for Nonwoven Sheet Materials of Comparative Examples H and I and Examples 17–20

| Ex. | Process Sequence | Pattern | Fiber Weight (g/m$^2$) | Binder Weight (g/m$^2$) | Pattern Embossing Conditions (° C. - N/mm$^2$ - m/min) | Smooth-Role Calender Conditions (° C. - N/mm$^2$ - m/min) |
|---|---|---|---|---|---|---|
| C.H | PR (Web A) | G | 20 | 20 | 188 - 2.03 - 13 | Not Applicable |
| 17 | SPR (Web A) | G | 20 | 20 | 188 - 2.03 - 13 | 156 - 1.37 - 13 |
| C.I | PR (Web A) | A | 30 | 20 | 188 - 2.03 - 13 | Not Applicable |
| 18 | SPR (Web A) | A | 30 | 20 | 188 - 2.03 - 13 | 156 - 1.37 - 13 |
| 19 | SPR (Web B) | A | 30 | 20 | 152 - 1.37 - 9.1 | 154 - 1.37 - 9.1 |
| 20 | SRP (Web B) | A | 30 | 20 | 152 - 1.37 - 9.1 | 154 - 1.37 - 9.1 |

Comparative Examples J and K
and
EXAMPLES 21–24

Comparative Examples J and K and Examples 21–24 multilayer laminates were made from the nonwoven sheet materials of Comparative Examples H and I and Examples 17–20 to provide Comparative Examples J and K and Examples 21–24, respectively. Each multilayer laminate was made by sandwiching polypropylene film between two nonwoven sheets, resulting in the arrangement of nonwoven sheet/tie layer/nonwoven sheet. The three layer sample was then placed between the platens (15.2 cm×15.2 cm) of a preheated Carver press (machine No. 2824-1; Fred S. Carver, Inc., Menomonee Falls, Wis.) at 0.6 MPa for 30 seconds at 182° C. The polypropylene film (a 0.4 mm blown XBP-486.0; obtained from Consolidated Film, Chippewa Falls, Wis.) served as a tie layer to bond the two nonwoven sheets.

Evaluations

The multilayer laminates described in Comparative Examples J and K and Examples 21–24 were cut into appropriate sample sizes and evaluated (machine direction and cross-direction) for tensile strength at break and for tear propagation.

Tensile strength were measured using an Instron tensile testing machine, Model 1122 (Instron Corp., Canton, Mass.) equipped with a 45 N load cell, model 2511-105 (full scale range assembly A40-41 A). A cross-head speed of 12.7 cm/min and a 5-cm gap were used for all testing. Samples measuring 12.7 cm×1.27 cm were conditioned for at least four hours at constant temperature (20° C.) and humidity (50%) conditions prior to being tested at the conditioning environment.

Tear testing in both the MD and CD directions was done using an Elmendorf tester (Thwing Albert Instrument Co, Model 60-200) according to ASTM D1922. Samples cut at 6.35 cm×6.35 cm were conditioned as described for tensile strength measurement, placed in the jaws of the tester, and clamped. An initial slit was made before the pendulum was released. The test measured the force required to propagate a straight tear with the requirement that the tear not deviate more than 6.4 mm from the initial cut.

The results are shown in Table 6. All samples were observed to be hand-tearable and to provide a fairly clean, straight tear in the cross-direction with minimal fraying. All samples were suitable for use as backings for masking tapes; the samples had sufficient tensile strength to enable them to be pulled through dried paint without delaminating or tearing and were sufficiently nonporous to prevent paint solvents from penetrating through the backing to the adhesive.

Conclusions

The test results provided in Table 6 show that the hand-tearable, multilayer laminates of the present invention (all made with resin-bonding, pattern-embossing, and smooth-roll calendering process steps) had improved tensile strength when compared with corresponding laminates made without a smooth-roll calendering process step (Comparative Examples J and K). Example 21, for example, showed a 20% increase over Comparative Example J in MD tensile while maintaining good hand tearability in the CD direction.

It should be understood from these examples that a wide range of desirable physical properties could be achieved by tailoring the carded nonwoven web fiber, the binder, the adhesive chemistry and coating weight, and the processing conditions (web forming, calender temperatures, calender roll materials and patterns, etc.) to meet a particular end-use objective.

The complete disclosures of all patents, patent applications, and publications are herein incorporated by reference as if individually incorporated. It is to be understood that the above description is intended to be illustrative, and not restrictive.

Various modifications and alterations of this invention will become apparent to those skilled in the art from the foregoing description without departing from the scope and the spirit of this invention. It should be understood that this invention is not to be unduly limited to the illustrative embodiments set forth herein.

What is claimed is:

1. A pressure-sensitive adhesive article comprising:
    a nonwoven backing having a first surface and a second surface; and
    a pressure sensitive adhesive coated on the first surface of the backing, wherein the backing comprises an embossed pattern on a fibrous web, wherein the embossed pattern is selected from the group consisting of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction, wherein the embossed pattern causes the web to tear in a substantially straight line.

2. A nonwoven sheet article comprising an embossed pattern on a fibrous web selected from the group consisting

TABLE 6

Evaluation Results for Multilayer Laminates of Comparative Examples J and K and Examples 21–24

| Ex. | Process Sequence | Pattern | Tensile Strength MD (N/cm) | | | Tensile Strength CD (N/cm) | | | Tear (MD) (g/16 ply) | | | Tear (CD) (g/16 ply) | | |
|---|---|---|---|---|---|---|---|---|---|---|---|---|---|---|
| | | | N | Avg. | SD | N | Avg. | SD | N | Avg. | SD | N | Avg. | SD |
| C.J | PR Web A | G | 3 | 21.5 | 0.3 | 3 | 14.2 | 0.6 | 2 | 109 | 1 | 2 | 108 | 3.3 |
| 21 | SPR Web A | G | 3 | 27.8 | 0.7 | 3 | 19.4 | 0.2 | 1 | 140 | — | 3 | 130 | — |
| C.K | PR Web A | A | 3 | 23.5 | 0.6 | 3 | 15.2 | 0.1 | 2 | 130 | 6 | 2 | 102 | 2 |
| 22 | SPR Web A | A | 3 | 27.7 | 0.4 | 3 | 26.4 | 0.7 | 1 | 173 | — | 1 | 109 | — |
| 23 | SPR Web B | A | 3 | 38.6 | 0.9 | 3 | 27.3 | 0.4 | 3 | 120 | 16 | 3 | 99 | 9 |
| 24 | SRP Web B | A | 3 | 44.1 | 1.0 | 3 | 33.8 | 0.4 | 3 | 124 | 7 | 3 | 99 | 5 | of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction, wherein the embossed pattern causes the web to tear in a substantially straight line.

3. The article according to claim 1, wherein the fibrous web comprises nonfracturable staple fibers, binder fibers, and a binding agent.

4. The article according to claim 2, wherein the fibrous web comprises nonfracturable staple fibers, binder fibers, and a binding agent.

5. The article according to claim 1, wherein the plurality of depressions is up to about 28% of a total surface area of the backing.

6. The article according to claim 2, wherein the plurality of depressions is up to about 28% of a total surface area of the backing.

7. The article according to claim 1, further comprising a low adhesion backsize composition coated on the second surface of the backing.

8. The article according to claim 1, further comprising a release liner on the pressure sensitive adhesive coated on the first surface of the backing.

9. The article according to claim 1, wherein each of the plurality of depressions is in a shape selected from the group consisting of a diamond, a rectangle, a circle, an oval, a triangle, a "+" sign, a "<" sign, a ">" sign, and a combination thereof.

10. The article according to claim 2, wherein each of the plurality of depressions is in a shape selected from the group consisting of a diamond, a rectangle, a circle, an oval, a triangle, a "+" sign, a "<" sign, a ">" sign, and a combination thereof.

11. The article according to claim 1, wherein the distance between two consecutive depressions in a first direction is about 0.51 mm to about 0.36 mm and the distance between two consecutive depressions in a second direction is about 0.51 mm to about 0.36 mm.

12. The article according to claim 2, wherein the distance between two consecutive depressions in a first direction is about 0.51 mm to about 0.36 mm and the distance between two consecutive depressions in a second direction is about 0.51 mm to about 0.36 mm.

13. The article according to claim 1, wherein the each of the first direction and the second direction are substantially normal to one another.

14. The article according to claim 2, wherein the each of the first direction and the second direction are substantially normal to one another.

15. The article according to claim 1, wherein each of the plurality of depressions in a row is in a shape selected from the group consisting of alternating "+" signs and "−" signs.

16. The article according to claim 2, wherein each of the plurality of depressions in a row is in a shape selected from the group consisting of alternating "+" signs and "−" signs.

17. The article according to claim 1, wherein the pressure sensitive adhesive is selected from the group consisting of a rubber-based adhesive, a water-based adhesive, a solvent-based adhesive, a hot-melt adhesive, and a combination thereof.

18. The article according to claim 1, wherein each of the plurality of depressions is about 15% to about 22% of a total surface area of the backing.

19. The article according to claim 2, wherein each of the plurality of depressions is about 15% to about 22% of a total surface area of the backing.

20. The article according to claim 1, wherein the plurality of depressions is a combination of a "+" sign and a "−" sign and the plurality of depressions is about 15% to about 20% of a total surface area of the backing.

21. The article according to claim 2, wherein the plurality of depressions is a combination of a "+" sign and a "−" sign and the plurality of depressions is about 15% to about 20% of a total surface area of the backing.

22. The article according to claim 1, wherein the plurality of depressions is a combination of a "+" sign and a "−" sign such that the plurality of depressions is about 15% to about 20% of a total surface area of the backing.

23. The article according to claim 2, wherein the plurality of depressions is a combination of a "+" sign and a "−" sign such that the plurality of depressions is about 15% to about 20% of a total surface area of the backing.

24. The article according to claim 1, wherein the backing further comprises a second nonwoven web.

25. A method for making a nonwoven sheet material comprising:

forming a randomly interlaced fibrous web of tensilized nonfracturable staple fibers and binder fibers;

pattern embossing the fibrous web with a pattern selected from the group consisting of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction;

subsequent to pattern embossing, smooth roll calendering the fibrous web; and subsequent to smooth roll calendering, uniformly interbonding the fibrous web throughout using a chemical binding agent.

26. The method according to claim 25, wherein the interbonding step comprises infusing the fibrous web with a water-based chemical binding agent.

27. The method according to claim 26, further comprising drying the fibrous web infused with the water-based chemical binding agent until substantially all the water is removed.

28. The method according to claim 25, further comprising coating a layer of pressure sensitive adhesive on a first surface of the fibrous web.

29. The method according to claim 25, further comprising coating a low adhesion backsize on a second surface of the fibrous web.

30. A method for making a nonwoven sheet material comprising:
  forming a randomly interlaced fibrous web of tensilized nonfracturable staple fibers and binder fibers;
  first smooth roll calendering the fibrous web;
  pattern embossing the fibrous web with a pattern selected from the group consisting of at least two rows of a plurality of depressions in a first direction aligned to form columns of the plurality of depressions in a second direction, wherein a distance between two depressions in one column varies from a distance between two depressions in a second column, and at least two rows of a plurality of depressions in a first direction aligned to form columns of the plurality of depressions in a second direction, wherein a distance between two depressions in at least one column varies along the first direction; and
  uniformly interbonding the fibrous web throughout using a chemical binding agent, wherein smooth roll calendering is performed prior to pattern embossing or uniformly interbonding.

31. The method according to claim 30, wherein the interbonding step comprises infusing the fibrous web with a water-based chemical binding agent.

32. The method according to claim 31, further comprising drying the fibrous web infused with the water-based chemical binding agent until substantially all the water is removed.

33. The method according to claim 30, further comprising coating a layer of pressure sensitive adhesive on a first surface of the fibrous web.

34. The method according to claim 33, further comprising winding the fibrous web in a roll such that the pressure sensitive adhesive on the first surface of the fibrous web contacts a low adhesion backsize on the second surface of the fibrous web.

35. The method according to claim 30, further comprising coating a low adhesion backsize on a second surface of the fibrous web.

36. The method according to claim 30, wherein uniformly interbonding is performed prior to pattern embossing.

37. The method according to claim 30, wherein pattern embossing is performed prior to uniformly interbonding.

38. A method of making a pressure-sensitive adhesive article comprising:
  forming a first randomly interlaced fibrous web;
  smooth roll calendering the fibrous web;
  pattern embossing the fibrous web to form an embossed pattern comprising a plurality of discontinuous depressions in a first direction and a second direction;
  uniformly interbonding the fibrous web throughout using a chemical binding agent; and coating a first surface of the fibrous web with a pressure sensitive adhesive, wherein the pressure sensitive adhesive article has an Overtaping value of less than about 76 mm.

39. The method of claim 38, further comprising laminating a second fibrous web to the first fibrous web.

40. The method of claim 38, further comprising coating a low adhesion backsize on a second surface of the fibrous web.

41. The method of claim 38, wherein pattern embossing the fibrous web occurs prior to smooth roll calendering the fibrous web and uniformly interbonding the fibrous web.

42. The method of claim 38, wherein smooth roll calendering the fibrous web occurs prior to pattern embossing the fibrous web and uniformly interbonding the fibrous web.

43. The method of claim 41, wherein uniformly interbonding the fibrous web occurs prior to pattern embossing the fibrous web.

44. A method for making a nonwoven sheet material comprising:
  forming a randomly interlaced fibrous web comprising a first major surface and a second major surface, wherein the fibrous web comprises a longitudinal axis and a width generally perpendicular to the longitudinal axis;
  pattern embossing the fibrous web with a repeating pattern, the repeating pattern comprising:
    a plurality of first depressions forming a plurality of first columns aligned with the longitudinal axis, and
    a plurality of second depressions forming a plurality of second columns aligned with the longitudinal axis, wherein the plurality of first columns and the plurality of second columns alternate across the width of the fibrous web, and further wherein each first depression in the plurality of first depressions comprise a shape different than a shape of each second depression in the plurality of second depressions;
  smooth roll calendaring the fibrous web;
  uniformly interbonding the fibrous web throughout using a chemical binding agent; and coating the first major surface of the fibrous web with a pressure sensitive adhesive.

45. The method according to claim 44, wherein uniformly interbonding the fibrous web comprises infusing the fibrous web with a water-based chemical binding agent.

46. The method according to claim 44, wherein each first depression in the plurality of first depressions is selected from the group consisting of diamonds, rectangles, circles, ovals, triangles, "+" signs, "<" signs, ">" signs, and combinations thereof.

47. The method according to claim 44, wherein each first depression in the plurality of first depressions comprises a "+" sign and each second depression in the plurality of second depressions comprises a "–".

48. The method according to claim 44, wherein each first depression in the plurality of first depressions comprises a "–" sign and each second depression in the plurality of second depressions comprises a "|".

49. A method for making a pressure-sensitive adhesive article comprising:
  forming a first randomly interlaced fibrous web comprising a first major surface and a second major surface, wherein the fibrous web comprises a longitudinal axis and a width generally perpendicular to the longitudinal axis;
  smooth roll calendaring the fibrous web;
  pattern embossing the fibrous web to form a repeating pattern, the repeating pattern comprising:
    a plurality of first depressions forming a plurality of first columns aligned with the longitudinal axis, and
    a plurality of second depressions forming a plurality of second columns aligned with the longitudinal axis, wherein the plurality of first columns and the plurality of second columns alternate across the width of the fibrous web, and further wherein each first depression in the plurality of first depressions comprise a shape different than a shape of each second depression in the plurality of second depressions;
  uniformly interbonding the fibrous web throughout using a chemical binding agent; and coating the first major surface of the fibrous web with a pressure sensitive adhesive, wherein the pressure sensitive adhesive article has an Overtaping value of less than about 76 mm.

50. The method according to claim 49, further comprising laminating a second fibrous web to the first fibrous web.

51. The method according to claim 49, wherein each first depression in the plurality of first depressions is selected from the group consisting of diamonds, rectangles, circles, ovals, triangles, "+" signs, "<" signs, ">" signs, and combinations thereof.

52. The method according to claim 49, wherein each first depression in the plurality of first depressions comprises a "+" sign and each second depression in the plurality of second depressions comprises a "−".

53. The method according to claim 49, wherein each first depression in the plurality of first depressions comprises a "−" sign and each second depression in the plurality of second depressions comprises a "|".

54. A method for making a pressure-sensitive adhesive article comprising:

forming a first randomly interlaced fibrous web comprising a first major surface and a second major surface, wherein the fibrous web comprises a longitudinal axis and a width generally perpendicular to the longitudinal axis;

pattern embossing the fibrous web with a repeating pattern, the repeating pattern comprising a plurality of depressions forming a plurality of columns aligned with the longitudinal axis and a plurality of rows across the width of the nonwoven backing, wherein the plurality of depressions comprises "+" signs;

smooth roll calendaring the fibrous web; and uniformly interbonding the fibrous web throughout using a chemical binding agent.

55. The method according to claim 54, wherein uniformly interbonding the fibrous web comprises infusing the fibrous web with a water-based chemical binding agent.

56. The method according to claim 54, wherein each first depression in the plurality of first depressions is selected from the group consisting of diamonds, rectangles, circles, ovals, triangles, "+" signs, "<" signs, ">" signs, and combinations thereof.

57. The method according to claim 54, wherein each first depression in the plurality of first depressions comprises a "+" sign and each second depression in the plurality of second depressions comprises a "−".

58. The method according to claim 54, wherein each first depression in the plurality of first depressions comprises a "−" sign and each second depression in the plurality of second depressions comprises a "|".

* * * * *

UNITED STATES PATENT AND TRADEMARK OFFICE
CERTIFICATE OF CORRECTION

PATENT NO.    : 6,383,958 B1
DATED         : May 7, 2002
INVENTOR(S)   : Swanson, David P.

It is certified that error appears in the above-identified patent and that said Letters Patent is hereby corrected as shown below:

Column 19,
Line 23, "N/mm" should read -- $N/mm^2$ --.

Signed and Sealed this

Eighteenth Day of February, 2003

JAMES E. ROGAN
*Director of the United States Patent and Trademark Office*